US006476048B1

(12) United States Patent
Szabo et al.

(10) Patent No.: US 6,476,048 B1
(45) **Date of Patent: *Nov. 5, 2002**

(54) SUBSTITUTED PHENANTHRIDINONES AND METHODS OF USE THEREOF

(75) Inventors: Csaba Szabo, Gloucester, MA (US); Prakash Jagtap, Beverly, MA (US); Garry Southan, Salem, MA (US); Andrew Salzman, Belmont, MA (US)

(73) Assignee: Inotek Pharamaceuticals Corporation, Beverly, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/602,539

(22) Filed: Jun. 22, 2000

Related U.S. Application Data

(63) Continuation-in-part of application No. 09/587,181, filed on Jun. 2, 2000, now abandoned, and a continuation-in-part of application No. 09/454,867, filed on Dec. 7, 1999, now Pat. No. 6,297,990.

(51) Int. Cl.[7] .................... A61K 31/473; A61K 31/47; C07D 221/12; C07D 217/00

(52) U.S. Cl. .................... 514/309; 514/319; 514/331; 514/298; 546/141; 546/146; 546/143; 546/108

(58) Field of Search .................... 514/309, 319, 514/331, 298, 316; 546/141, 146, 143, 108

(56) References Cited

U.S. PATENT DOCUMENTS

| | | | | |
|---|---|---|---|---|
| 3,291,801 A | | 12/1966 | Montgomery | 260/289 |
| 3,932,643 A | * | 1/1976 | Gauthier | 424/258 |
| 5,519,053 A | | 5/1996 | Kun et al. | 314/457 |
| 5,552,267 A | | 9/1996 | Stern et al. | 435/1.1 |
| 5,583,155 A | | 12/1996 | Kun et al. | 514/457 |
| 5,587,384 A | | 12/1996 | Zhang et al. | 514/309 |
| 5,621,104 A | | 4/1997 | Graham et al. | 546/108 |
| 5,908,861 A | | 6/1999 | Kun | 514/456 |
| 6,121,278 A | | 9/2000 | Jackson et al. | 514/292 |
| 6,197,785 B1 | | 3/2001 | Jackson et al. | 514/309 |
| 6,235,748 B1 | | 5/2001 | Li et al. | 514/285 |
| 6,291,425 B1 | | 9/2001 | Li et al. | 514/81 |
| 6,346,536 B1 | | 2/2002 | Li et al. | 514/286 |
| 6,348,475 B1 | | 2/2002 | Zhang et al. | 514/309 |
| 6,358,975 B1 | | 3/2002 | Eliasson et al. | 514/309 |
| 2001/0020013 A1 | | 9/2001 | Zhang et al. | 514/150 |
| 2002/0006927 A1 | | 1/2002 | Li et al. | 514/253.03 |
| 2002/0019417 A1 | | 2/2002 | Zhang et al. | 514/307 |
| 2002/0022636 A1 | | 2/2002 | Li et al. | 514/307 |
| 2002/0028813 A1 | | 3/2002 | Jackson et al. | 514/248 |
| 2002/0028815 A1 | | 3/2002 | Ator et al. | 514/249 |
| 2002/0037904 A1 | | 3/2002 | Li et al. | 514/288 |

FOREIGN PATENT DOCUMENTS

| | | | |
|---|---|---|---|
| EP | 0 638 309 A1 | | 2/1995 |
| WO | WO 99/08680 | | 2/1999 |
| WO | WO 99/11622 | | 3/1999 |
| WO | WO 99/11623 | | 3/1999 |
| WO | WO 99/11624 | | 3/1999 |
| WO | 9911624 | * | 3/1999 |
| WO | WO 99/11628 | | 3/1999 |
| WO | WO 99/11644 | | 3/1999 |
| WO | WO 99/11645 | | 3/1999 |
| WO | WO 99/11649 | | 3/1999 |
| WO | WO 99/36402 | | 7/1999 |
| WO | WO 99/59973 | | 11/1999 |
| WO | WO 99/59975 | | 11/1999 |
| WO | WO 00/39070 | | 7/2000 |
| WO | WO 00/39104 | | 7/2000 |
| WO | WO 00/42040 | | 7/2000 |
| WO | WO 01/21615 | | 3/2001 |

OTHER PUBLICATIONS

Cookson M.R. et al., "J. Neurochem." ;70/2,501–508(1998); Peroxynitrile & Hydrogen Peroxide . . . role of ADP–rib.*

Weltin et al., "Int'l J.Radiat.Biol.";72/6,685–692(1997);Effect of 6(5H)–phenanthridinone–PARS.*

Banisk M. and Ueda K., Mole. Cell. Biochem. 138:185–197 (1994).

Griffin et al., J. Med. Chem. 41:5247–5256 (1998).

White et al., J. Med. Chem. 43:4084–4097 (2000).

Bowes et al. Inhibitors of poly (ADP–ribose) synthetase protect rat cardiomyocytes against oxidant stress. *Cardiovasc Res.* 1999;41:126–134.

Cozzocrea et al. Beneficial effects of 3–aminobenzamide, an inhibitor of poly (ADP–ribose) synthetase in a rat model of splanchnic artery occlusion and reperfusion. *Br J Pharmacol.* 1997;121:1065–1074.

Docherty et al. An inhibitor of poly (ADP–ribse) synthetase activity reduces contractile dysfunction and preserves high energy phosphate levels during reperfusion of the ischemic rat heart. *Br J Pharmacol.* 1999;127:1518–1524.

Grupp et al. Protection against hypoxia–reoxygenation in the absence of poly (ADP–ribose) synthetase in isolated working hearts. *J Mol Cell Cardiol.* 1999;31:297–303.

Szabo et al. Poly (ADP–ribose) polymerase inhibition reduces reperfusion injury after heart transplantation. *Cir Res.* 2002;90:100–106.

Szabo et al. Inhibition of poly (ADP–ribose) synthetase exerts anti–inflammatory effects and inhibits neutrophil recruitment. *J Exp Med.* 1997;186:1041–1049.

Thiemermann et al. Inhibition of the activity of poly (ADP ribose) synthetase reduces ischemia–reperfusion injury in the heart and skeletal muscle. *Proc Natl Acad Sci USA.* 1997;94:679–683.

(List continued on next page.)

*Primary Examiner*—Richard L. Raymond
*Assistant Examiner*—Sudhaker B. Patel
(74) *Attorney, Agent, or Firm*—Pennie & Edmonds LLP

(57) ABSTRACT

This invention provides a novel class of substituted 6(5H) phenanthridinone compounds. Pharmaceutical compositions, and methods of making and using the compounds, or a pharmaceutically acceptable salt, hydrate, prodrug, or mixture thereof are also described.

59 Claims, 6 Drawing Sheets

OTHER PUBLICATIONS

Zingarelli et al. Protection against myocardial ischemia and reperfusion injury by 3–aminobenzamide, an inhibitor of poly (ADP ribose) synthetase. *Cardiovasc Res.* 1997;36:205–215.

Andrievskii, et al., Chem. Heterocycl. Compds. (English Transl.), 21, 924–931 (1985).

Banasik, et al., J. Biol. Chem., 267, 1569–1575 (1991).

Migachev & Terent'ev, Chem. Heterocycl. Compds. (English Transl.), 17,394–397 (1981).

Nemeth, et al., Eur. J. Pharmacol, 339, 215–221 (1997).

Szabo, Shock, 6, 79–88 (1996).

Szabo & Dawson, Trends Pharmacol. Sci., 19, 287–298 (1998).

Taylor & Strojny, J. Am. Chem. Soc., 78, 5104–5108 (1956).

Virag and Szabo, Br. J. Pharmacol., 126, 769–777 (1999).

Crowley, et al., Journal of Pharmacology, 259:78–85 (1991).

Weltin, et al., International Journal of Radiation Biology, 72:685–692 (1997).

* cited by examiner

SUBSTITUTED PHENANTHRIDINONES AND METHODS OF USE THEREOF

RELATED APPLICATIONS

This application is a continuation-in-part to U.S. Ser. No. 09/454,867 filed Dec. 7, 1999, now issued as U.S. Pat. No. 6,297,990, and U.S. Ser. No. 09/587,181, filed Jun. 2, 2000 now abandoned. The contents of these applications are incorporated by reference herein in their entireties.

STATEMENT OF GOVERNMENT INTEREST

This invention was made with the support of the federal government under grant number R01HL59266 awarded by the National Institutes of Health. The government has certain rights in the invention.

BACKGROUND OF THE INVENTION

Inflammation disorders, such as arthritis, colitis, and autoimmune diabetes, typically manifest themselves as disorders distinct form those associated with reperfusion injury, e.g., stroke and heart attack, and can clinically manifest themselves as different entities. However, there can be common underlying mechanisms between these two types of disorders. In particular, inflammation and reperfusion injury can induce proinflammatory cytokine and chemokine synthesis. Induction of pro-inflammatory cytokines can, in turn, result in production of cytotoxic free radicals such as nitric oxide and superoxide. NO and superoxide can react to form peroxynitrite ($ONOO^-$) (Szabó et al., Shock 6:79–88, 1996).

The peroxynitrite-induced cell necrosis observed in inflammation and reperfusion injury involves, in significant part, the activation of the nuclear enzyme poly (ADP-ribose) synthetase (PARS). Activation of PARS is thought to be an important step in the cell-mediated death observed in inflammation and reperfusion injury (Szabó et al., Trends Pharmacol. Sci. 19: 287–98, 1998).

SUMMARY OF THE INVENTION

The invention is based in part on the discovery of novel substituted 6(5H)phenanthridinone derivatives and their unexpected effects in inhibiting inflammation, in treating reperfusion injuries, and in reducing the severity of diabetes.

Accordingly, in one aspect the invention provides novel substituted 6(5H)phenanthridinone derivatives falling within formula I, as set forth in the Detailed Description of the Invention, below.

Also provided is a method of treating inflammatory and reperfusion conditions in mammals by administering to a mammal in need of such treatment an effective amount of a compound according to formula I.

In a further aspect, the invention also includes a method for the production of compounds of formula I.

The substituted 6(5H)phenanthridinone compounds of the invention are potent, pharmaceutical compounds that can be used to treat a variety of conditions and diseases, typically those known to involve inflammatory mediator production and cell death.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

Figure 1A:
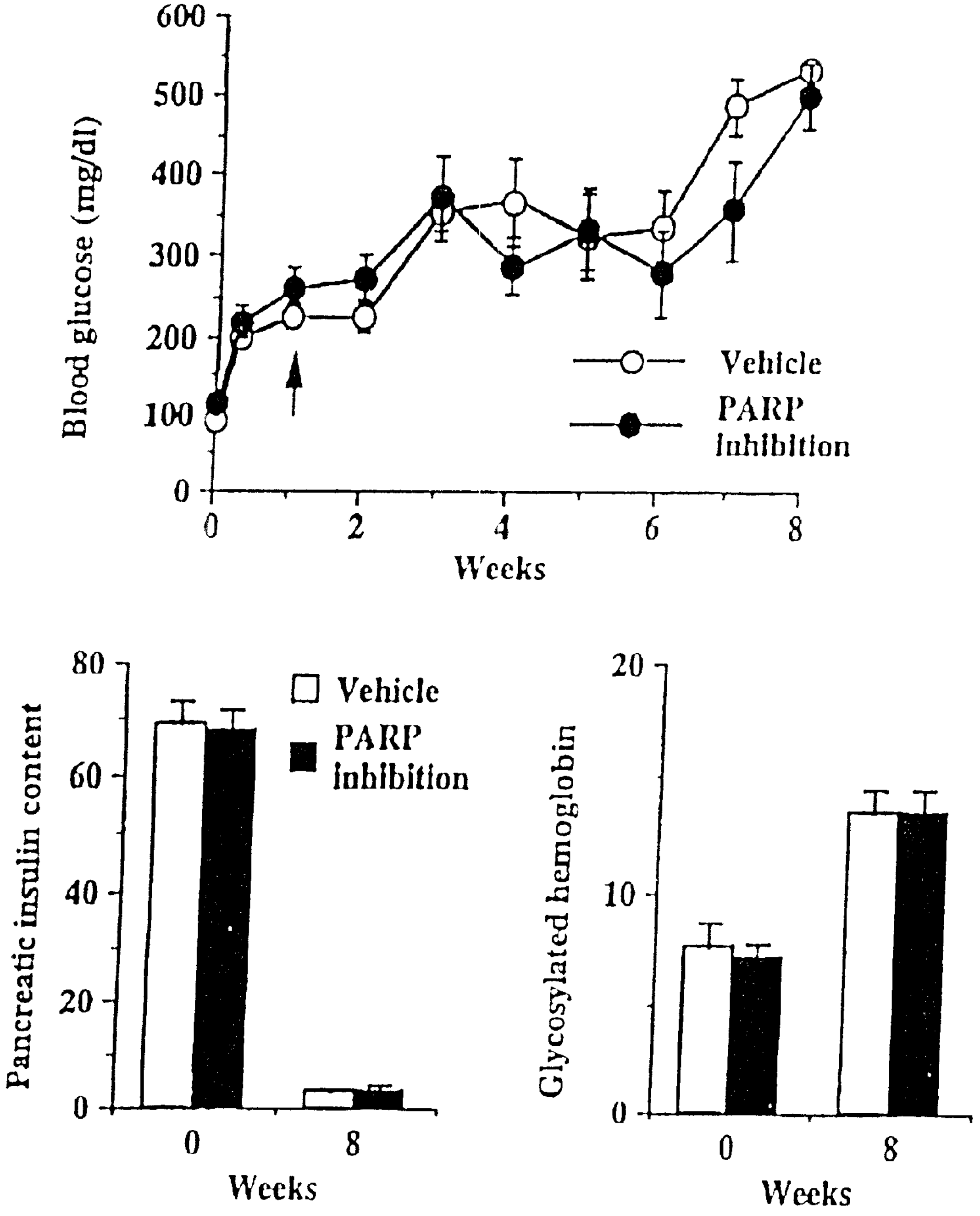
FIGS. 1A and 1B are graphs and histograms showing levels of blood glucose, insulin, glycosylated hemoglobin, and acetylcholine-induced relaxation of thoracic aortic rings in streptozotocin treated mice treated with vehicle or the PARS inhibitor PJ34.

The present invention provides a novel class of 2-substituted 6(5H)phenanthridinone compounds falling within the formula I, as set forth below:

I

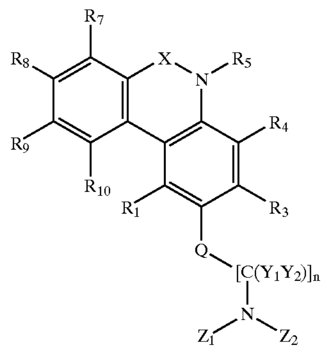

where

X is C═O, C═S, $SO_2$, C═NH, C═$NR_6$; C—Cl

Q is NHCO, O, CO, $OCO_2$, OCO, OCONH, $NR_2$, $NHCO_2$, S, $SO_2$, CS, SO;

$R_1$, $R_3$, $R_4$, $R_5$, $R_6$, $R_7$, $R_8$, $R_9$, $R_{10}$, are, independently, hydrogen or lower alkyl; halogen, nitro, amino, alkylamino, carboxy, ester $Y_1$ and $Y_2$ are, independently: hydrogen, halo, alkylhalo, hydroxy, $C_1$–$C_{10}$ straight or branched chain alkyl, $C_2$–$C_{10}$ straight or branched chain alkenyl group, $C_3$–$C_8$ carbocyclic, aryl, alkylamino, amino, carboxy, ester, arylalkyl, nitro;

n is 0 to 10; and $Z_1$ and $Z_2$ are, independently: hydrogen, alkylhalo, aklylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein the ring has 4–8 ring members.

In addition to the compounds of Formula I, the invention also provides a pharmaceutically acceptable base or acid addition salt, hydrate, ester, solvate, prodrug, metabolite, stereoisomer, or mixture thereof. The invention also includes pharmaceutical formulations comprising a compound of Formula I in association with a pharmaceutically acceptable carrier, diluent, or excipient.

As used herein:

"Alkyl" refers to saturated or unsaturated branched or straight chain hydrocarbon radical. Typical alkyl groups include methyl, ethyl, propyl, isopropyl, butyl, isobutyl, tertiary butyl, pentyl, hexyl and the like.

"Alkylhalo" refers an alkyl group containing a halogen substituent; "alkylhydroxy" refers to an alkyl group having a hydroxyl substituent; "alkylamino" refers to an alkyl group having an amino substituent; "alkylester" refers to an alkyl group having an ester functionality appended thereto; "alkylcarboxy" refers to an alkyl group having a carboxyl functionality appended thereto.

"Alkenyl" refers to unsaturated branched or straight chain hydrocarbon radical, having at least one carbon-carbon double bond.

"Alkynyl" refers to unsaturated branched or straight chain hydrocarbon radical having at least one carbon-carbon triple bond.

"Alkoxy" refers to the radical —O-alkyl. Typical alkoxy radicals are methoxy, ethoxy, propoxy, butoxy and pentoxy and the like.

"Cycloalkyl" refers to saturated monocyclic hydrocarbon radical containing 3–8 carbon atoms such as cyclopropyl, cyclobutyl, cyclopentyl, cyclohexyl, cycloheptyl, cyclooctyl, and the like.

"Aryl" refers to unsaturated cyclic, hydrocarbon radical.

"Substituted phenyl" refers to all possible isomeric phenyl radicals such as mono or disubstituted with a substituent selected from the group consisting of alkyl, alkoxy, hydroxy, or halo.

"Halo" refers to chloro, fluoro, bromo or iodo.

The carrier must be "acceptable" in the sense of being compatible with the active ingredient of the formulation and not deleterious to the subject to be treated. Preferably, the carrier is also capable of stabilizing the compound or composition.

Whenever the term "alkyl" or its prefix root appears in a name of a substituent (e.g. aralkoxyaryloxy) it shall be interpreted as including those limitations given above for "alkyl".

In some embodiments, X is C═O.

In some embodiments, one or more $R_1$, $R_3$, $R_4$, $R_5$, $R_6$, $R_7$, $R_8$, $R_9$, $Y_1$, or $Y_2$ are hydrogen.

In some embodiments, is NHCO.

In some embodiments, n is 1.

In some embodiments, one or both of $Z_1$ and $Z_2$ are methyl groups (PJ-34).

In some embodiments, one or both of $Z_1$ and $Z_2$ are ethyl groups (PJ-44).

In some embodiments, $Z_1$ is a methyl group and $Z_2$ is a benzyl group (PJ-45).

In some embodiments, N, $Z_1$ and $Z_2$ taken together, form piperidine, piperazine, N-alkylated or alkylcarbonylated piperazine, pyrole, imidazole, indole, or other $C_2$ to $C_{10}$ branched or cyclic or cycloalkenyl amines.

In some embodiments, $Z_1$, N, and $Z_2$ taken together form a fused ring having six ring members.

In some embodiments, $Z_1$ and $Z_2$ taken together form $—CH_2—CH_2—CH_2—CH_2—CH_2—$ (PJ-36).

In some embodiments, at least one of the ring members is oxygen.

In some embodiments, $Z_1$ and $Z_2$ taken together form $—CH_2—CH_2—O—CH_2—CH_2—$ (PJ-38).

In some embodiments, two of the ring members are nitrogen atoms.

In some embodiments, $Z_1$ and $Z_2$ taken together form $—CH_2—CH_2—N(CH_3)—CH_2—CH_2—$ (PJ-46).

In particularly preferred embodiments, the compounds have the structures represented by PJ 34, 36, 38, 44 and 46.

PJ34

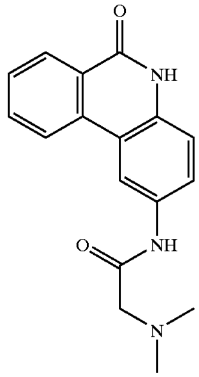

PJ36

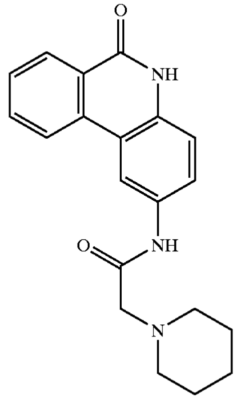

PJ38

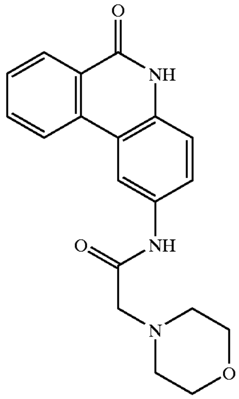

-continued

PJ44

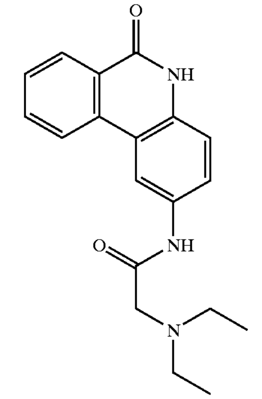

PJ46

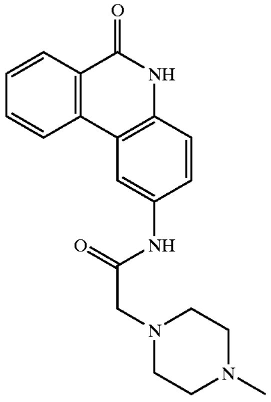

Salts encompassed within the term "pharmaceutically acceptable salts" refer to non-toxic salts of the compounds of this invention which are generally prepared by reacting the free base with a suitable organic or inorganic acid to produce "pharmaceutically-acceptable acid addition salts" of the compounds described herein. These compounds retain the biological effectiveness and properties of the free bases. Representative of such salts are the water-soluble and water-insoluble salts, such as the acetate, amsonate (4,4-diaminostilbene-2, 2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, maleate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

Methods of using substituted 6(5H)phenanthridinone derivatives

The invention also includes a method of inhibiting poly (ADP)-ribose synthase activity (PARS) in a cell. This enzyme, which is also known as poly(ADP-ribose) synthetase and PARS (poly(ADP-ribose) polymerase, EC 2.4.99), and ADP-ribosyltransferase (ADPRT, EC 2.4.2.30), is a nuclear enzyme that catalyzes a transfer of the ADP ribose moiety of NAD+ to an acceptor protein.

The method includes contacting the cell with a compound of formula I in an amount sufficient to inhibit poly (ADP)-ribose-synthase in the cell. In general, any cell having, or capable of having, PARS activity, can be used. The can be provided in any form so long as it is accessible to the compound. For example, the cell can be provided in vitro, ex vivo, or in vivo. PARS activity can be measured using any method known in the art, e.g., methods as described in Banasik et al., *J. Biol. Chem.* 267:1569–75, (1991).

Also provided in the invention is a method of inhibiting, preventing, or treating inflammation in a subject. The inflammation can be associated, e.g., with an inflammatory disease. Inflammatory diseases refer to diseases or conditions where there is an inflammation of the body tissue. These include local inflammatory responses and systemic inflammation. Examples of such diseases and conditions include: transplant rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gum, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used cancer chemotherapy.

The invention also includes a method of treating, preventing, or otherwise inhibiting reperfusion injury in a subject in need of treatment, prevention, or inhibition thereof. The method includes administering a compound of formula I in an amount sufficient to inhibit reperfusion injury in the subject. Reperfusion refers to the process whereby blood flow in the blood vessels is resumed after blood flow has been interrupted, such as occurs following constriction or obstruction of the vessel. Reperfusion is typically associated with ischemia and may result following a naturally occurring episode, such as a myocardial infarction or stroke, or during a surgical procedure where blood flow in vessels is purposely or unintentionally blocked off.

Also included in the invention is a method for treating or preventing diabetes in a subject. In another aspect, the invention provides a method for treating complications, e.g., vascular complications, associated with diabetes by administering a PARS inhibitor.

Patients with advanced Type I or Type II diabetes mellitus frequently suffer from associated retinopathy and peripheral vascular disease. Diabetic vasculopathy also predisposes a subject for accelerated atherosclerosis and hypertension, and is a significant risk factor for end-stage renal disease, coronary atherosclerosis, and cerebrovascular disease. Tooke et al., Diabet. Med. 16: 710–5, 1999; Keen et al., Diabetes Metab. Res. Rev. 15: 186–96, 1999. Endothelial injury and dysfunction is a critical constituent of diabetic vasculopathy. Tooke et al., Diabet. Med. 16: 710–5, 1999; Keen et al., Diabetes Metab. Res. Rev. 15: 186–96, 1999. Oxygen-derived free radicals and oxidants play an important role in the pathogenesis of endothelial dysfunction. Rodriguez-Manas L et al., Br. J. Pharmacol. 123: 1495–502, 1998; Graier et al., Diabetes Res. Clin. Pract. 45:153–60, 1999; Nishikawa et aL, Nature 404: 787–90, 2000. Oxidant mediated cell death and dysfunction have recently been linked to activation of the nuclear enzyme poly(ADP-ribose) polymerase (PARP). Szabo and Dawson, Trends Pharmacol. Sci. 19: 287–98, 1998; Pieper et al., Trends Pharmacol. Sci. 20: 171–81, 1999.

While not wishing to be bound by theory, it is believed that activation of PARP is an important factor in the pathogenesis of endothelial dysfunction in diabetes. Destruction of functional islet cells with streptozotocin in mice induces chronic hyperglycemia, intravascular production of oxidants, activation of PARP in the endothelium, and a loss of endothelial function. Treatment with a novel potent phenanthridinone PARS inhibitor, starting after the time of islet destruction, was observed to maintain normal vascular responsiveness. This responsiveness was maintained despite the persistence of severe hyperglycemia. Human and murine endothelial cells incubated in high glucose medium exhibited prolonged PARP activation, which was due to the intracellular production of reactive nitrogen and oxygen species. Vascular rings from $PARP^{+/+}$ mice incubated in high glucose medium showed a loss of endothelial function, an effect prevented by pharmacological inhibition of PARP and did not develop in the vascular rings from $PARP^{-/-}$ mice. Thus, PARS activation is implicated in the pathogenesis of diabetic endothelial dysfunction.

Diabetic vascular dysfunction is a major clinical problem, which predisposes to a variety of cardiovascular diseases. Hyperglycemic episodes are thought to play a major role in the development of the endothelial dysfunction, which represents a major component of diabetic vasculopathy. Tooke et al., Diabet. Med. 16: 710–5, 1999; Keen et al., Diabetes Metab. Res. Rev. 15: 186–96, 1999; Rodriguez-Manas L et al., Br. J. Pharmacol. 123: 1495–502, 1998; Graier etal., Diabetes Res. Clin. Pract. 45:153–60, 1999; Nishikawa et al., Nature 404: 787–90, 2000. The reduced production of nitric oxide from the vascular endothelial cells in diabetes predisposes to platelet and neutrophil deposition, vasospasm, hypertension, stroke and myocardial infarction, as well as accelerated atherosclerosis. The generation of intracellular oxidants within the mitochondria of the diabetic endothelium, and in the vicinity of endothelium, plays a key role in the loss of endothelial function in diabetes; Nishikawa et al., Nature 404: 787–90, 2000.

Accordingly, the invention includes a method of treating or preventing diabetes by administering to a subject in need thereof an amount of an inhibitor of a poly (ADP-Ribose) polymerase (PARS) sufficient to lessen or prevent the symptoms of diabetes in the subject. The compound preferably acts by inhibiting PARS in the subject. In some embodiments, the PARS inhibitor is a compound of Formula I, as described above. In other emboeiments, the inhibitor can be, e.g., benzamide, 3-aminobenzamide, nicotinamide, 4-aminobenzamide, and 1,5, dihydroxy-isoquinoline. In some embodiments, administering the inhibitor does not increase insulin levels in the subject.

The method can be used to treat a subject that has, e.g., Type I or Type II diabetes, and/or any conditions or diseases associated with diabetes. The conditions or diseases can include, e.g., the diseases related to cardiovascular complications of type I or Type II diabetes. Examples of such disease include, e.g., retinopathy, nephropathy, peripheral vascular disease, vascular aneurysm, limb ischemia, ischemia-related limb gangrene, ulcers—including diabetic foot ulcer- and skin lesions, claudication, autonomic nervous system dysfunction, peripheral neuropathy, organic impotence, accelerated atherosclerosis, cardiomyopathy, myocardial dysfunction, ischemia and infarction, cerebrovascular disease.

The invention also provides a method of increasing or maintaining vascular responsiveness, e.g., appropriate contractile and endothelium-dependent relaxant responsiveness, in an endothelial cell. In some embodiments, the endothelial cell is provided in a blood vessel. The cell can be provided, e.g., in vitro, ex vivo, or in vivo. For example, the method can include administering to a subject in need thereof an amount of an inhibitor of a poly (ADP-Ribose) polymerase (PARs) in an amount sufficient to inhibit activation of PARS in said subject. The inhibitor can be, e.g., a PARS inhibitor according to Formula I, as described above. Alternatively, or in addition, the inhibitor can be, e.g., benzamide, 3-aminobenzamide, nicotinamide, 4-aminobenzamide, and 1,5, dihydroxy-isoquinoline.

Additionally, the invention provides a method of enhancing the function of a transplanted organ in a subject, e.g., a human subject.

For example, the method can include administering to a subject a poly (ADP-Ribose) polymerase (PARS) inhibitor in an amount sufficient to enhance the function of the transplanted organ in the subject. The inhibitor can be, e.g., a PARS inhibitor according to Formula I, as described above. Alternatively, or in addition, the inhibitor can be, e.g., benzamide, 3-aminobenzamide, nicotinamide, 4-aminobenzamide, and 1,5, dihydroxy-isoquinoline. In some embodiments, the organ is contacted with the inhibitor prior to transplantation. In other embodiments, the inhibitor is administered to the subject at the time of transplantation of the organ.

The method is useful for enhancing the function of a variety of transplanted organs, including, but not limited to, heart, kidney, lung, liver, retina, pancreatic islet, blood vessel, skin, and bone.

In some embodiments, a PARS inhibitor is used in combination with an immuno-suppressant. Suitable immunosuppressants include, e.g., cyclosporine, tacrolimus, mycophenolate mofetil, corticosteroids, azathioprine, and mixtures thereof.

In addition to, or instead of an immuno-suppressant, the inhibitors of the invention may be used with an organ preservative solution, or a mixture of organ preservation and cardioplegic solutions.

Generally, current donor organ preservation protocols utilize hypothermic (below 20° C. and typically at about 4° C.) arrest and storage in a chemical perfusate for maintaining the heart (non-beating) or other organ (non-functioning) for up to four hours. However, these protocols utilize a variety of crystalloid-based cardioplegic solutions that do not completely protect the donor heart from myocardial damage resulting from ischemia and reperfusion injuries. In addition to myocardial damage, ischemia, reperfusion and/or increased potassium concentrations may also cause coronary vascular endothelial and smooth muscle injury leading to coronary vasomotor dysfunction, which is believed to be the leading cause of late organ failure. Additionally, significant medical advantages would be achieved if organs for transplantation could be stored and preserved for 2–3 days and longer. Longer storage times provide additional time for histocompability testing of the donor and recipient, organ viability testing and provides additional time for preoperative decisions and preparations.

Numerous preservative solutions have been developed and used to preserve major organs while they are in cold storage prior to their transplantation. Optimal preservation solution s include those which minimize ischemic and/or reperfusion injuries, minimize cell swelling and edema; prevent intracellular acidosis; and provide substrates for regeneration of high-energy phosphate compounds and ATP during reperfusion. The most commonly used preservation solutions for transplantation include crystalloid cardioplegia consisting of isotonic or slightly hypertonic saline supplemented with glucose and potassium chloride of which buffering capacity is usually afforded by the addition of sodium bicarbonate. In addition, some solutions contain small amounts of magnesium or calcium, glucose, ATP and creatine phosphate, while others contain pharmacologic agents such as mannitol, insulin, procaine or calcium channel blockers. See, e.g, U.S. Pat. Nos. 5,066,578, 6,046,046, 6,037,116. See also, U.S. Pat. No. 5,552,267 for disclosure on preservation solutions containing a phosphodiesterase inhibitor.

Typical organ preservative solutions include, without limitation, University of Wisconsin (UW) or Belzer's solution (U.S. Pat. No. 4,798,824) which is marketed by DuPont as VIASPAN™ solution; Marshall's preservation fluid; histidine-tryptophan-alpha-ketoglutarate solution (Kallerhoff et al., Transplantation 39:485–489 (1985)); Phosphate buffered extracellular (Ep4) solution (Handa et al., J. Exp. Med. 159:205 (1988)); St. Thomas solution; Columbia solution (U.S. Pat. No. 5,552,267), CMH solution (Arita et al., Transplant Proc. 5:336 (1992)), and Stanford solution (Swanson et al., J of Heart Transplant. 7:456–467 (1988)).

Other widely used preservative flush solutions which are commercially available are the Collins (Collins, The Lancet 1219–1222 (1969)) and the Euro-Collins (Squifflet et al, Transplant. Proc. 13:693–696 (1981)) solutions. These solutions resemble intracellular fluid and contain glucose as an osmotic agent. In addition to glucose, high osmolality preservative solutions have been prepared using raffinose and lactobionate as in the UW preservative solution (Ploeg et al., Transplant. Proc., 20 (suppl 1) 1:935–938 (1988); U.S. Pat. No. 4,798,824), mannitol in the Sacks solution (Sacks, The Lancet 1:1024–1028 (1973)), sucrose in the phosphate buffered sucrose (PBS) preservative solution (Lam et al, Transplantation 47:767–771 (1989)) and the histidine buffered HTK solution of Bretschneider (Kallerhoff et al., Transplantation 39:485–489 (1985)). Hypertonic citrate preservative solutions are also known. Ross et al., Transplantation 21:498–501 (1976). The effectiveness of these solutions as preservative solutions for organs appears to be related to the specific osmotic agent which is used. Coffey and Andrews, Transplantation 35:136–143 (1983). Preservative solutions are also known which contain synthetic hydroxyethyl starch (HES) as an osmotic colloid. See, e.g., U.S. Pat. Nos. 4,879,283, 4,798,824, and 5,082,831.

Preservative solutions are also known for preserving corneas for transplantation. Corneal preservative solutions are designed to prevent endothelial cell damage. Corneal preservative solutions containing glucose or dextran are known. Kaufman et al., Arch. Ophthalmol 109:864–868 (1991); McCarey and Kaufman Invest. Ophthalmol. 13: 165 and 859 (1974). The corneal preservative solutions known as OPTISOL™, DEXSOL™ and MK™ contain DEXTRAN 40 (average molecular weight=40,000 daltons) as an osmotic agent. U.S. Pat. No. 5,306,711 discloses preservative solutions containing dextran having an average molecular weight of 10,000 daltons or less. U.S. Pat. No. 5,145,771 describes a storage solution for preserving organs at temperatures between 0 and 37° C. U.S. Pat. No. 5,693,462 discloses organ preservation solutions containing compounds such as amiloride and derivatives thereof which are useful for inhibiting $Na^+/H^+$ exchange. The preservation solutions described therein include a balanced isotonic solution of sodium, potassium, calcium, and magnesium ions and bicarbonate in a physiologically acceptable amount, and an amiloride-containing compound. The amiloride-containing compound may be amiloride, hexamethylene amiloride, dimethyl amiloride, ethyl isopropyl amiloride or methyl isobutyl amiloride. The preserving solutions may also include other components such as EDTA, a small amount of adenosine, and at least one antioxidant, such as, dimethyl thiourea (DMTU), catalase as a hydrogen peroxide scavenger and apoferritin to decrease iron content within the preservation solution. In addition, the preservation solutions optionally may include hormones, such as insulin and prostaglandin and antibiotics.

The inhibitors of the invention are also useful for enhancing the function of a transplanted organ. For example, prior to transplanting an organ into a patient, the organ is contacted with a compound of the invention in an amount sufficient to inhibit PARS in the organ. Additionally, the inhibitors of the invention can be used to prolong the function of a transplanted organ in a subject. For example, the method can include administering to the subject a poly (ADP-Ribose) polymerase (PARS) inhibitor in an amount sufficient to inhibit PARS in said subject before, during, or after the transplant operation.

The subject in the above-mentioned methods can be, e.g., a mammal, e.g., a human, mouse, rat, dog, cat, horse, cow, pig, or non-human primate. Administration can be systemic or topical, and can be prophylactic or therapeutic.

The term "pharmacologically effective amount" means that amount of a drug or pharmaceutical agent that will elicit the biological or medical response of a tissue, system, animal or human that is being sought by a researcher or clinician.

The invention also includes pharmaceutical compositions suitable for inhibiting or preventing inflammation or reperfusion injury, PARS activity, or more than one of these activities. The compositions are preferably suitable for internal use and include an effective amount of a pharmacologically active compound of the invention, alone or in combination, with one or more pharmaceutically acceptable carriers. The compounds are especially useful in that they have very low, if any toxicity.

In practice, the compounds or their pharmaceutically acceptable salts, are administered in amounts which will be sufficient to inhibit inflammatory conditions or disease and/ or prevent the development of inflammation or inflammatory disease in animals or mammals, and are used in the pharmaceutical form most suitable for such purposes.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Administration of the active compounds and salts described herein can be via any of the accepted modes of administration for therapeutic agents. These methods include systemic or local administration, such as intravenous, intraperitoneal, intramuscular, intraventricular, subcutaneous, topical, sublingual, oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active compound or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One approach for parenteral administration employs the implantation of a slow-release or sustained-released systems, which assures that a constant level of dosage is maintained, according to U.S. Pat. No. 3,710,795, incorporated herein by reference.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the present invention range from 0.002 mg to 50 mg per kg of body weight per day.

Compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Any of the above pharmaceutical compositions may contain 0.1–99%, preferably 1–70% of the active compounds, especially compounds of the Formula I as active ingredients.

Also within the invention is a method of identifying a candidate agent for treating diabetic vascular complications. The method includes contacting a PARS enzyme with a test compound with the PARS enzyme within endothelial or smooth muscle cells, and determining whether the compound inhibits the activity of said enzyme. An inhibition of PARS activity in the presence of the compound indicates the test agent is a candidate agent for treating diabetes, and/or for treating vascular dysfunction.

Synthesis of novel phenanthridinones

The substituted 6(5H)phenanthridinone compounds described herein can be prepared by methods well known in the art. Additional exemplary synthetic routes for compounds having the general structure of formula II, which describes compounds encompassed by Formula I, are illustrated as Scheme I and Scheme II, below.

In Scheme I, a 9-fluorenone (A) is treated with sulfuric acid and aqueous sodium azide in a ring-expansion, or Schmidt, reaction to produce 6(5H)-phenanthridinone (B). Nitration of (B) produces 2-nitro-6(5H)-phenanthridinone (C) as a major product, which is then reduced by Fe, $NH_4Cl$ and DMF, or catalytic dehydrogenation, to produce 2-amino-6(5H)-phenanthridinone (D). In general, a compound falling within Formula II is prepared by modifying the parent molecule 6(5H)-Phenanthridinone. See, e.g., U.S. Pat. Nos. 3,291,801 and 3,932,643; Taylor et al., *J. Am. Chem. Soc.* 78:5104–5108 (1956). The 2-nitro (Compound C)-and 2-amino (Compound D)-6(5H)-phenanthridinones are synthesized by a slight modification of procedures described in Andrievskii, et al., *Chem. Heterocycl. Compds* (*English Transl.*) 21:8, 924–931 (1985), and Migachev, et al. *Chem. Heterocycl. Compds* (*English Transl.*) 17:3, 394–397 (1981)

Compound (E) is generated by acylating compound (D) with an appropriate halo-acylhalide. A compound falling within Formula II is then formed by the addition of a secondary amine.

In Scheme II, 2-amino-9-fluorenone (compound (F)) is acylated with a halo-acylhalide to produce the N-acylated compound (G). The central ring of compound (G) is then expanded in a Schmidt reaction as described for Scheme I. The ring opening reaction produces a mixture of compounds: the 2-substituted compounds according to Formula II are the major component of the mixture, while the 8-substituted compounds (H) are the minor component of the mixture.

Scheme I

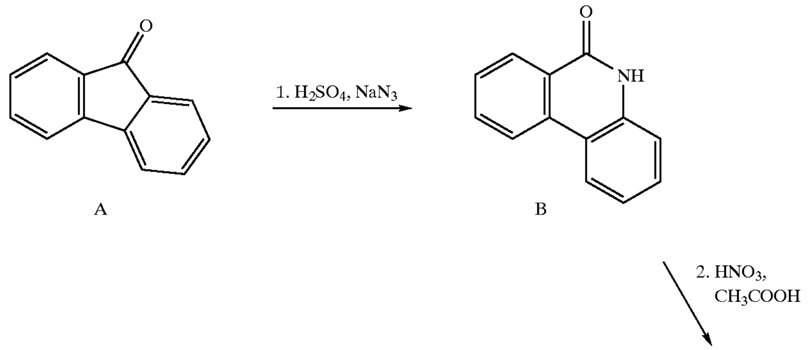

A

B

-continued
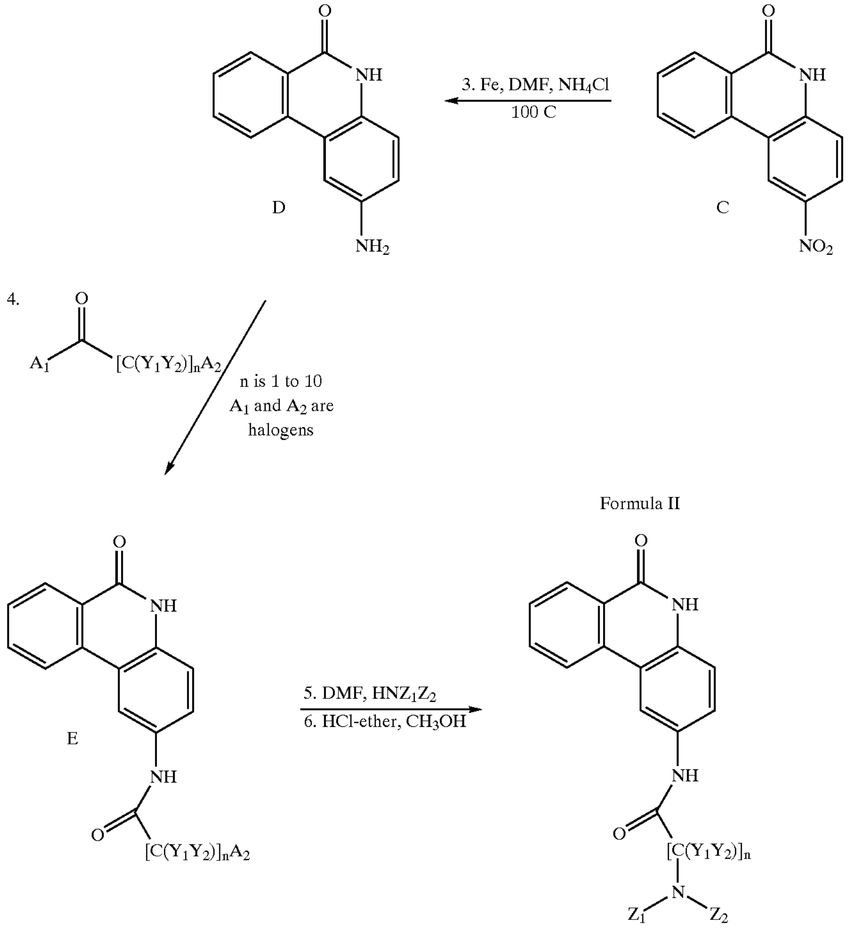
D C E Formula II
Scheme II
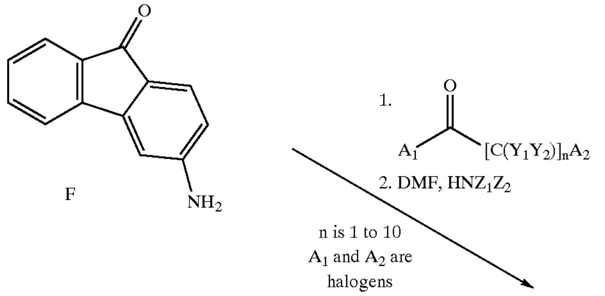
F

-continued

G

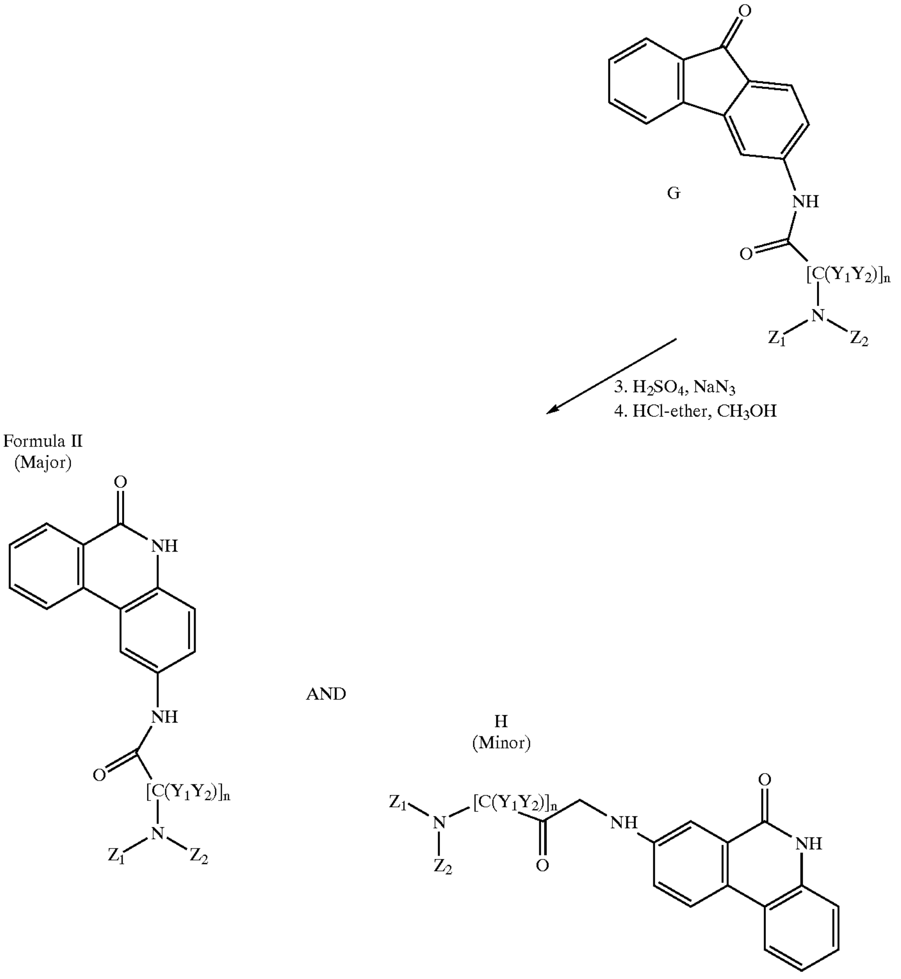

Formula II (Major)

AND

H (Minor)

EXAMPLES

The invention will be further described in the following examples, which do not limit the scope of the invention described in the claims. The following examples illustrate the synthesis of novel substituted 6(5H)phenanthridinone derivatives of the invention and of their use to inhibit inflammation and reperfusion, and of the effects of substituted phenanthridinones on vascular function in vitro, and in vivo in murine diabetes models.

Example 1

Synthesis of Novel Substituted Phenanthridinones (Scheme I)

Synthesis of 6(5H)-phenanthridinone

6(5H)-Phenanthridinone was prepared by the method described by Gauthier in U.S. Pat. No. 3,932,643. Briefly, to a well stirred solution of 9-fluorenone (15 g, 0.083 mol) in concentrated sulfuric acid (500 mL), sodium azide (8.1 g, 0.12 mol) was slowly added over a period of 3 hr at 0° C. The reaction mixture was stirred at room temperature for 2 hr, until nitrogen no longer evolved. The reaction mixture was then poured slowly over crushed ice, to produce a solid precipitate which was filtered and washed thoroughly with cold water to remove sulfuric acid. The solid was then dried under vacuum, to give pure 6(5H)-phenanthridinone (15 g, 93%).

Synthesis of 2-Nitro-6(5H)-phenanthridinones

2-Nitro and 2-amino-6(5H)-phenanthridinones were synthesized by slight modification in the procedure described by Andrievskii et al., *Chem. Heterocycl. Compds* (*English Transl.*) 21:8, 924–931 (1985) and by Migachev et al., *Chem. Heterocycl. Compds* (*English Transl.*) 17:3, 394–397 (1981). Briefly, to a well stirred solution of 6(5H)-phenanthridinone (4.5 g, 0.023 mol) in acetic acid (200 mL) nitric acid (10 mL) was added, and the reaction mixture was stirred at 100° C. for 2 hr. The solid that separated out was filtered and washed thoroughly with acetic acid and then by cold water to remove acidic impurities. The solid was then dried under vacuum, then recrystalized from DMF to give pure 2-nitro-6(5H)-phenanthridinone (3.8 g, 70%). The filtrate was diluted with cold water, and a yellow colored solid precipitated which was filtered and washed with water. The yellow solid was then dried under vacuum, and identified to be pure 4-nitro-6(5H)-phenanthridinone (650 mg, 12%).

Synthesis of 2-Amino-6(5H)-phenanthridinones

To a suspension of 2-nitro-6(5H)-phenanthridinone (3.8 g, 0.016 mol) in DMF (200 mL) was added an ammonium chloride solution (3%, 200 mL), followed by the addition of iron powder (22 g). The reaction mixture was stirred at 100° C. for 1 hr. The residue was removed by filtration, and the filtrate was made acidic by adding dilute HCl (25%, 20 mL).

A solid separated from the solution and was filtered and washed thoroughly with cold water to remove acidic impurities. The solid was then dried under vacuum, to give hydrochloride salt of 2-amino-6(5H)-phenanthridinone (3.4 g, 89%).

Synthesis of N-(6-oxo-5,6-dihydro-phenanthridin-2-yl)-chloroacetamide

To a suspension of HCl salt of 2-amino-6(5H)-phenanthridinone (3.4 g, 0.014 mol) in ethyl acetate (200 mL) was added saturated solution of sodium bicarbonate (200 mL), followed by addition of chloroacetyl chloride (5.6 mL, 0.07 mol). The reaction mixture was stirred at room temperature for 2 days. The solid that separated out was filtered and washed thoroughly with cold water. It was then dried under vacuum to give N-(6-oxo-5, 6-dihydro-phenanthridin-2-yl)-chloroacetamide (3.35 gm, 85%).

According to the methods illustrated above, by changing the identity of the secondary amine, a number of different N,N-disubstituted compounds were produced. Representative compounds are shown in Table 1.

Specifically, PJ34 was prepared as follows:

A suspension of 2-nitro-6(5H)-phenanthridinone in DMF was reduced by iron and ammonium chloride to produce 2-amino-6(5H)-phenanthridinone. Chloroacylation of 2-amino-6(5H)-phenanthridinone with chloroacetyl chloride in pyridine/DMF yielded N-(6-oxo-5,6-dihydro-phenanthridin-2-yl)-chloroacetamide, which then was treated with dimethyl amine in methanol or with N,N-dimethylformamide to furnish the N-(6-oxo-5,6-dihydro-phenanthridin-2-yl)-N,N-dimethylacetamide. This latter compound was then treated with HCl in ether in presence of methanol to give PJ34 as a water-soluble HCl salt. Product identity and purity were assessed using $^1$HNMR, MS, TLC and HPLC.

TABLE 1

| Compound | n | $Y_1$ | $Y_2$ | $Z_1$ | $Z_2$ |
|---|---|---|---|---|---|
| PJ-34 | 1 | H | H | $—CH_3$ | $—CH_3$ |
| PJ-44 | 1 | H | H | $—CH_2CH_3$ | $—CH_2CH_3$ |
| PJ-36 | 1 | H | H | $—CH_2CH_2CH_2CH_2CH_2—$ | |
| PJ-38 | 1 | H | H | $—CH_2CH_2OCH_2CH_2—$ | |
| PJ-46 | 1 | H | H | $—CH_2CH_2N(CH_3)CH_2CH_2—$ | |

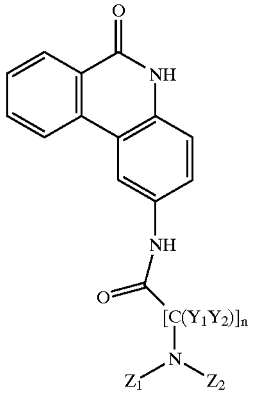

Example 2

Alternate Synthesis of Novel Substituted Phenanthridinones (Scheme II)

Synthesis of N-(6-oxo-5,6-dihydro-phenanthridin-2yl)-choroacetamide

To a supension of HCl salt of 2-amino-6(5H)-phenanthridinone (100 mg, 0.04 mmol) in DMF (5 mL), pyridine (0.5 mL) was added, followed by the addition of chloroacetyl chloride (0.2 mL, 0.002 mol) at 0° C. The reaction mixture was stirred at room temperature for 1 to 2 hrs. It was then poured over crushed ice, and the solid obtained was washed thoroughly with cold water. The solid was then dried under vacuum to give N-(6-oxo-5,6-dihydro-phenanthridin-2-yl)-choroacetamide (95 mg, 84%).

Synthesis of N-(6-oxo-5–6-dihydro-phenantridin-2-yl)-N, N-dimethylacetamide

To a solution of N-(6-oxo-5, 6-dihydro-phenanthridin-2-yl)-chloroacetamide (1.5 g, 0.0052 mol) in DMF (10 mL) a solution of dimethyl amine in methanol (20 mL) was added. The reaction mixture was stirred at room temperature for 3 hours. The solid that separated out was filtered and washed thoroughly with cold water. It was then dried under vacuum and recrystalized from methanol/ether to give N-(6-oxo-5, 6-dihydro-phenanthridin-2-yl)-N,N-dimethylacetamide. This compound was dissolved in methanol (25 rub) and treated with a solution of HCl in ether (2 M, 5 mL). The solid was filtered and washed thoroughly with dry ether, and recrystalized from methanol/ether to provide the hydrochloride salt of N-(6-oxo-5, 6-dihydro-phenanthridin-2-yl)-N, N-dimethylacetamide (1.4 g, 81%).

Synthesis of 2-(N-chloroacetyl)-9-fluorenone

A saturated solution of sodium bicarbonate (5 mL) was added to a solution of 2-amino-9-fluorenone (190 mg, 0.97 mmol) in ethyl acetate (5 mL). Next, chloroacetyl chloride (0.4 mL, 4.8 mmol) was added, and the reaction mixture was stirred at room temperature for 1 hour. The ethyl acetate layer was separated, and washed thoroughly with cold water. It was then dried under vacuum to give 2-(N-chloroacetyl)-9-fluorenone (185 mg, 70%).

Synthesis of 2-[N-(2-N,N-dimethylaminoacetyl)]-9-fluorenone

To a solution of 2-(N-chloroacetyl)-9-fluorenone (185 mg, 0.68 mmol) in DMF (5 mL) a solution of dimethyl amine in methanol (5 mL) was added. The reaction mixture was stirred at room temperature for 1 hour. The reaction mixture was then poured over crushed ice and extracted in ethyl acetate (25 mL), washed thoroughly with cold water, dried over $Na_2SO_4$ then evaporated under vacuum to give 2-[N-(2-N,N-dimethylaminoacetyl)]-9-fluorenone (190 mg, 99%).

Synthesis of N-(6-oxo-5,6-dihydro-phenanthridin-2-yl)-N,N-dimethylacetamide

To a well stirred solution of 2-[N-(2-N,N-dimethylaminoacetyl)]-9-fluorenone (190 mg, 0.67 mmol) in concentrated sulfuric acid (5 mL), sodium azide (45 mg, 1.2 mmol) was added at 0° C., and the reaction mixture was stirred at room temperature until nitrogen no longer evolved. The reaction was then poured slowly over an ice-cold $K_2CO_3$ solution, followed by extraction with ethyl acetate (25 mL). The ethyl acetate layer was washed thoroughly with cold water, dried over sodium sulfate, and concentrated under vacuum. The resulting residue was purified by PTLC (silica gel, 1000 μM) to give a mixture of N-(6-oxo-5,6-dihydro-phenanthridin-8-yl)-N,N-dimethylacetamide (52 mg, 26%) and N-(6-oxo-5,6-dihydro-phenanthridin-2-yl)-N, N-dimethylacetamide (78 mg, 39%).

Example 3

Effects of Substituted Phenanthridinones on in vitro Inflammation Models

In in vitro studies, J774 macrophages were exposed to bacterial lipopolysaccharide (LPS), to induce pro-inflammatory mediator production and cytotoxicity. In this assay, the PJ compounds tested (PJ 34, 36, 38, 44 and 46) inhibited the production of the pro-inflammatory cytokine tumor necrosis factor alpha (TNF-α), the production of the pro-inflammatory chemokines macrophage inhibitory factor-1α and -2 (MIP-1α and MIP-2), as well as the production of the pro-inflammatory free radical nitric oxide (or NO, measured here as nitrite). Furthermore, the compounds restored the viability of the cells, which was suppressed in response to LPS exposure. This assay (the LPS-stimulated macrophage) represents an in vitro model of an inflammatory situation. Agents that block inflammatory mediator production in this assay are expected to have anti-inflammatory or immunosuppressive effects in inflammatory or immune diseases.

The half-maximal inhibitory effect (in μM) of various PJ compounds was assessed under a variety of conditions in immunostimulated J774 macrophages and in peroxynitrite-stimulated thymocytes. Macrophages or thymocytes were first treated with a chosen PJ compound for 30 min at a concentration ranging from 0.1 to 30 μM. The cells were then immunostimulated with LPS (10 μg/ml) or treated with peroxynitrite (30 μM). MIP production in the macrophages was measured at 3 h, TNF and nitric oxide were measured at 24 h, cell viability in the macrophages were measured at 24 h. PARS activation and cell death in thymocytes were measured at 6 h. Measurements of mediator production, PARS activation and cell death were essentially as described in Němeth, et al., Eur J Pharmacol 339:215–221 (1997) and Virăg and Szabó, Br J Pharmacol, 126: 769–777 (1999). Results in Table 2 are shown as EC50 values (half maximal inhibition of mediator production or restoration of cell viability; in μM): [mean±SEM of n=3–6 determinations].

centration range of 10 nM-1 μM. Agents that block PARS activation or cell death in this assay are expected to have cytoprotective effects in various diseases associated with reperfusion of ischemic organs.

Example 5

Effect of Substituted Phenanthridinones on in vivo Inflammation Models

In order to substantiate the efficacy of the PJ series of compounds in inflammatory conditions, the effect of compounds according to the invention were tested in a systemic inflammatory model induced by bacterial lipopolysaccharide. Injection of bacterial lipopolysaccharide (LPS) at high doses causes multiple organ dysfunction resembling of septic shock, and, ultimately, death. Agents that inhibit inflammatory mediator production, PARS activation, and cell death according to this model will prevent mortality induced by LPS. In experiments with Balb/c mice, injection of 90 mg/kg LPS intraperitoneally caused death in 92% of the animals over 24 h. However, pretreatment of the animals with 20 mg/kg PJ34 reduced the endotoxin-induced mortality to 50% under the same experimental conditions. In response to an even higher dose of LPS (120 mg/kg), PJ 34, 36, 38, 44 and 46, all injected at 10 mg/kg every 6 hours) caused an improvement in the endotoxin-induced mortality from 70% death to 30–40% death over 24 hours.

These data indicate that the PJ series of compounds have therapeutic effects in various systemic and local inflammatory conditions.

Example 6

Effect of Substituted Phenanthridinones on in vivo Reperfusion Injury Models

In order to substantiate the efficacy of the PJ series of compounds in ischemia-reperfusion conditions, the effect of the compounds in a local model of reperfusion injury

TABLE 2

| | Inhibition of TNF-α (J774) | Inhibition of MIP-1α (J774) | Inhibition of MIP-2 (J774) | Inhibition of Nitrite (J774) | Enhancement of cell Viability (J774) | Inhibition of PARS activation (thymocyte) | Enhancement of cell viability (thymocyte) |
|---|---|---|---|---|---|---|---|
| PJ 34 | 5.4 ± 0.6 | 10.2 ± 1.4 | 7.2 ± 0.88 | 15.2 ± 2.8 | 12.5 ± 1.4 | 0.3 ± 0.1 | 0.2 ± 0.1 |
| PJ 36 | 11.2 ± 1.1 | 15.2 ± 2.1 | 21.2 ± 2.7 | 25.4 ± 2.9 | 20.2 ± 2.3 | 0.2 ± 0.1 | 0.3 ± 0.1 |
| PJ 38 | 6.2 ± 0.42 | 11.3 ± 1.4 | 14.9 ± 1.3 | 20.2 ± 1.5 | 22.1 ± 2.7 | 0.8 ± 0.2 | 0.4 ± 0.2 |
| PJ 44 | 11.1 ± 0.67 | 10.2 ± 0.95 | 22.4 ± 1.2 | No effect | 16.2 ± 1.9 | 0.3 ± 0.1 | 0.2 ± 0.1 |
| PJ 46 | 9.2 ± 0.88 | >30 | >30 | >30 | >30 | 1 ± 0.3 | 1.3 ± 0.3 |

Example 4

Effects of Substituted Phenanthridinones on in vitro Reperfusion Injury Models

In additional in vitro studies in isolated thymocytes, cells were exposed to peroxynitrite or hydrogen peroxide (toxic oxidant species) to induce cytotoxicity. In this system, the toxicity is, at least partially, related to activation of the nuclear enzyme PARS (see Introduction). In this assay, the compounds of the invention (e.g., PJ 34, 36, 38, 44 and 46) inhibited the activation of PARS. Furthermore, the compounds prevented the oxidant-induced suppression of the viability of the cells (Table 2). The oxidant-stimulated thymocyte assay represents an in vitro model of a situation where cells are dying because of exposure to pro-oxidant species, as occurs in during the reperfusion of ischemic organs. A second experimental system was used where oxygen/glucose deprivation induced cell death in cultured neurons ( ie. an in vitro model of stroke). Here, PJ34 provided significant cytoprotection (up to 70%) in the coninduced by ligation and release of the coronary artery in an anesthetized rat was examined. In a model of 1-hour coronary ischemia, followed by reperfusion for 1 hour, treatment with PJ34 (5, g/kg i.v., injected 10 mm prior to the start of reperfusion), reduced myocardial infarct size development from 62±1 to 50±3% (area of necrosis, over area of risk). In addition, plasma levels of creatine phosphokinase (CPK, an indicator of myocardial necrosis) were reduced by PJ34 treatment by approx. 50%.

In another model, a mouse model of ischemic and reperfused gut was utilized. The superior mesenteric artery was occluded for 45 mm, followed by a reperfusion for 1 h. At the end of the reperfusion, gut permeability was measured with the PD4 method in evened gut sacks. Ischemia-reperfusion increased the permeability of the gut from 9±2 to 135±27 ml/min/$cm^2$, indicating of severe damage of the reperfused gut. Treatment with PJ 34 (5, g/kg i.v., injected 10 mm prior to the start of reperfusion), reduced the increase in the permeability of the gut to 41±12 mlmin/$cm^2$, indicating maintenance of the gut function. The ischemia-reperfusion studies in the gut were associated with a 38% mortality, whereas 100% survival was noted in the animals treated with PJ34. Similar protection was also observed with treatment with PJ36.

In another set of experiments, the effect of PJ34 in a rat model of middle cerebral artery occlusion/reperfusion was tested. Occlusion lasted for 2 hours, followed by reperfusion for 24 hours. Infarct size was quantified with the tetrazolium staining, and survival and neurological scores were monitored. PJ34 was administered at 10 mg/kg i.v. at 5 min before the start of reperfusion in one group, and at 2 h after the beginning of reperfusion in another group. Control or vehicle-treated animals developed a 73% mortality over 24 hours, whereas no animals died in the drug treated groups. PJ34, given at the time of reperfusion or at 2 h after the start of reperfusion reduced the size of brain infarction by 74±6 and 55±8%, respectively. Vehicle treated animals that survived for 24 h developed severe neurological deficit (4 on a scale of 1–4), whereas no detectable deficit was observed in the animals treated with PJ34.

These data indicate that the PJ series of compounds have therapeutic effects in various systemic and local conditions of ischemia-reperfusion.

Example 7

Effect of Substituted Phenanthridinone PJ34 in vivo on Vascular Function in a Murine Diabetes Model In the studies described in Examples 7 and Example 8, all materials were purchased from Sigma/Aldrich (St Louis, Mo.), unless specified otherwise.

Results are reported as mean±SEM of several experiments. Analysis of variance with Bonferroni's correction, or Student's t-test were used to compare mean values, as appropriate. Statistical differences were declared significant for $p<0.05$.

Male Balb/c mice were treated intraperitoneally (i.p.) with streptozotocin (240 mg/kg dissolved in citrate buffer) or vehicle (citrate buffer). Blood glucose was then monitored weekly over 8 weeks using a one-touch blood glucose meter (Lifescan). Hyperglycemia was defined as non-fasting blood glucose level higher than 200 mg/dL.

Total glycated hemoglobin (GHb) content of blood samples was measured using a commercially available kit (Sigma Diagnostics) according to manufacturers instructions. Blood (50 μl) was hemolyzed in 400 μl of hemolyzing reagent and 50 μl of the lysate was separated on an affinity resin column into wash fraction (W) containing non-glycated hemoglobin and elution fraction (E) containing glycated hemoglobin. The optical density of the two fractions were measured by spectrophotometry at 415 nm and the per cent glycated hemoglobin content was calculated as follows: GHb (%)=100E/(E+10W).

Samples of pancreas were removed on week 8 and weighed before being placed into 6 mls of acid ethanol (23:7:0.45, ethanol:$dH_2O$:HCl) and homogenized. The pancreas was incubated for 72 h at 4° C. before being centrifuged and the insulin content of the supernatant was determined using a commercially available ELISA kit (Alpco).

After eight weeks, diabetic mice (treated with vehicle or with PARS inhibitor) were killed and thoracic aortae cleared from periadvential fat, cut into small pieces (typically 4 pieces) and placed into chambers filled with warmed (37° C.), gas equilibrated (95% $O_2$, 5% $CO_2$) Krebs' solution: $CaCl_2$ 1.6 (mM), $MgSO_4$ 1.17 (mM), EDTA 0.026 (mM), NaCl 130 (mM), $NaHCO_3$ 14.9 (mM), KCl 4.7 (mM), $KH_2PO_4$ 1.18 (mM), glucose 11 (mM). Isometric tension was measured with isometric transducers (Kent Scientific Corporation, Litchfield, Conn.), digitized using a MacLab A/D converter and stored and displayed on a MacIntosh computer. The pre-load was 1 g and the aortic rings were equilibrated for 60 minutes, the solution was changed every 15 minutes. Dose-response curves to the endothelium-dependent relaxant acetylcholine ($10^{-9}$ to $3\times10^{-4}$ M) were performed in rings precontracted with phenylephrine ($10^{-6}$ M).

Complete destruction of pancreatic islet cells in mice was induced by treatment with high dose streptozotocin. This intervention induced a complete loss of pancreatic insulin content. Severe hyperglycemia ensued, which was persistent at plasma glucose levels of 250–350 mg/dl throughout the 8 weeks of the experiments (FIGS. 1A and 1B).

FIG. 1A shows blood glucose levels, blood glycosylated hemoglobin levels and pancreatic insulin content at 0–8 weeks after streptozotocin induced diabetes in male Swiss mice. Vehicle or PARS inhibitor treatment started at 1 week after streptozotocin (start of drug treatment indicated by an arrow), and continued throughout the experimental period. Drug treated animals were treated with 10 mg/kg PJ34 (per os), daily, once a day. At 8 weeks, blood was taken for measurement of glycosylated hemoglobin levels, pancreata taken for measurements of pancreatic insulin content, and thoracic aortae taken for determination of endothelium-dependent relaxant reactivity. There was no difference in the degree of hyperglycemia and glycosylated hemoglobin, and in the degree of pancreatic insulin loss between vehicle and PJ34 treated diabetic animals.

Figure 1B:
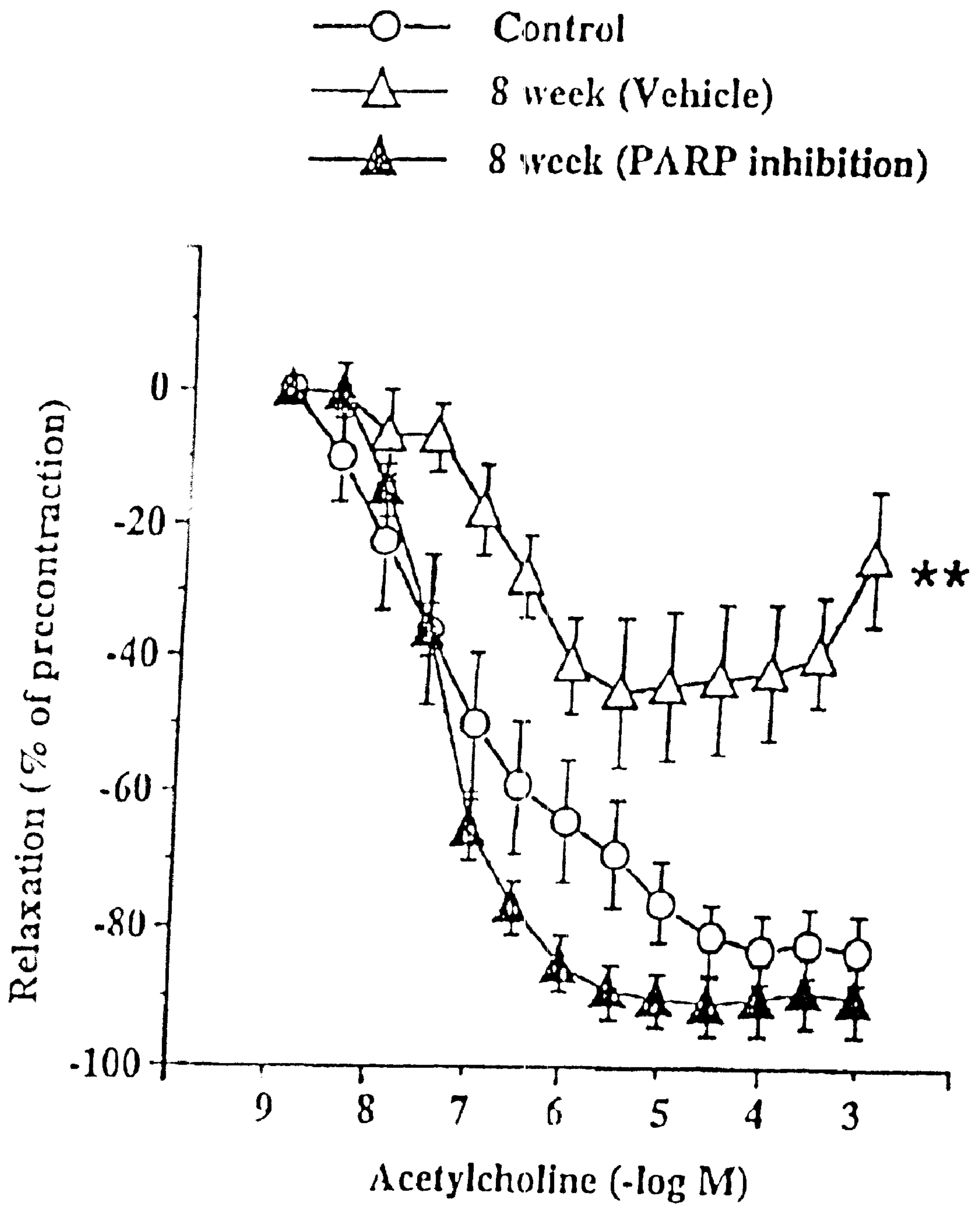

FIG. 1B demonstrates acetylcholine induced, endothelium-dependent relaxations in epinephrine-precontracted isolated thoracic aortic rings from animals which received no streptozotocin injection ("Control"), diabetic animals at 8 weeks treated with vehicle ("8 week—Vehicle"), and diabetic animals treated with PJ34 ("8 week—PARS inhibition"). There was a marked impairment of the endothelium-dependent relaxant ability of the vascular rings in diabetes, which was normalized in the animals where PARS was inhibited. Chronic treatment of normal (non-diabetic) mice with the PARS inhibitor (regimen as above) for 8 weeks did not affect the vascular reactivity (not shown). * * $P<0.01$ for vehicle-treated vs. PJ34 treated diabetic mice. N=8 animals or rings per group.

In a second group of mice, inhibition of PARS activation was achieved by chronic treatment with PJ34, starting at 1 week after the initiation of diabetes. After 8 weeks of hyperglycemia, there was an increase in immunostaining for nitrotyrosine (a reactive species produced from the reaction of superoxide and nitric oxide, in the vascular rings, and massive endothelial staining for poly(ADP-ribose), indicative of PARS activation. Ischiropoulos et al., Arch. Biochem. Biophys. 298: 431–7, 1992; Halliwell, FEBS Lett. 411: 157–60, 1997. Furthermore, ex vivo experiments demonstrated the loss of endothelial function, as measured by the relaxant responsiveness of pre-contracted vascular rings to the endothelium dependent vasodilator, nitric oxide liberating hormone acetylcholine (FIGS. 1A and 1B). Furchgott, Acta Physiol. Scand. 139: 257–70, 1990.

Immunohistochemical staining for nitrotyrosine, an indicator of generation of reactive nitrogen species, was also examined in control rings, in rings from diabetic animals treated with vehicle at 8 weeks, and in rings from diabetic animals treated with PJ34. There was a marked increase in tyrosine nitration in the diabetic rings, which was not affected by PJ34 treatment.

Immunohistochemical staining was also performed to look at levels of poly(ADP-ribose), an indicator of PARS activation. Staining was examined in control rings, in rings from diabetic animals treated with vehicle at 8 weeks, and in rings from diabetic animals treated with PJ34. There was a marked increase in PARS activation in diabetic endothelium, which was abolished by PJ34 treatment. Similar immunohistochemical profiles were seen in n=4–5 vascular rings in each experimental group.

Delayed treatment with a PARS inhibitor ameliorated poly(ADP-ribose) staining and restored normal vascular function in diabetic mice, without altering systemic glucose levels, plasma glycated hemoglobin levels, or pancreatic insulin content. Respective $EC_{50}$ values for acetylcholine amounted to 0.11±0.08 μM, 0.83±0.76 μM and 0.55±0.49 μM in control, diabetic and PJ34 treated diabetic rings, respectively. Thus, the $EC_{50}$ value of acetylcholine was not altered by PJ34, indicating that its protective effect is independent of altering the endothelial receptor sensitivity to acetylcholine.

Example 8

Effect of the Substituted Phenanthridinone PJ34 in vitro in Cells from $PARS^{+/+}$ and $PARS^{-/-}$ mice Human umbilical vein endothelial cells (HUVECs), and pulmonary endothelial cells generated from wild type and $PARS^{-/-}$ mice were placed in high glucose medium or an osmotically controlled normal glucose control.

Breeding pairs of mice for the PARS colony were a gift from Dr. Z. Q. Wang, International Agency for Research on Cancer Lyon, France. Thoracic aortae from $PARS^{-/-}$ and $PARS^{+/+}$ mice (Wang et al., Genes Dev.9: 509–20, 1995) were harvested, cleared of periadvential fat, and cut into 3 or 4 pieces. Rings were placed in tissue culture plates containing different media preparations (as below) and the plate was incubated at 37° C. and 5% $CO_2$ for 24 hours. Four different media preparations were used: a) normal glucose, i.e. 5 mM: in F-12K Nutrient Mixture medium (Gibco BRL—Life Technologies); b) Osmotic control, i.e. 30 mM L-glucose in F-12K medium; c) High glucose i.e. 30 mM D-glucose in F-12 K medium; and d) PARS inhibitor in the presence of high glucose: 3 μM PJ34 and 30 mM D-glucose in F-12K medium.

After incubation, aortic rings were mounted in organ baths filled with warmed and gas equilibrated Krebs' solution and endothelium dependent relaxant ability was evaluated as described above. Osmotic controls (30 mM L-glucose) were indistinguishable from normal glucose controls and are not presented in the figures.

To detect PARS, paraffin sections (3 μm) were deparaffinized in xylene and rehydrated in decreasing concentrations (100%, 95% and 75%) of ethanol followed by a 10 min incubation in PBS (pH 7.4). Sections were treated with 0.3% hydrogen peroxide for 15 min to block endogenous peroxidase activity and then rinsed briefly in PBS. Non-specific binding was blocked by incubating the slides for 1 h in PBS containing 2% horse serum. To detect poly(ADP-ribose), a routine histochemical procedure was applied, as previously described (Scott et al., Ann. Neurol. 45: 120–4, 1999) with minor modifications, as follows: Mouse monoclonal anti-poly(ADP-ribose) antibody (Alexis, San Diego, Calif.) and isotype-matched control antibody were applied in a dilution of 1:100 for 2 h at room temperature. Following extensive washing (5×5 min) with PBS, immunoreactivity was detected with a biotinylated goat anti-rabbit secondary antibody and the avidin-biotin-peroxidase complex (ABC), both supplied in the Vector Elite kit (Vector Laboratories, Burlingame, Calif.). Color was developed using Ni-DAB substrate (95 mg diaminobenzidine, 1.6 g NaCl, 2 g nickel sulfate in 200 ml 0.1M acetate buffer). Sections were then counterstained with nuclear fast red, dehydrated and mounted in Permount. Photomicrographs were taken with a Zeiss Axiolab microscope equipped with a Fuji HC-300C digital camera.

Detection of nitrotyrosine in aorta rings was carried out as described above for poly(ADP-ribose) staining except that rabbit anti-nitrotyrosine polyclonal antibody was used as the primary antibody. For nitrotyrosine staining of endothelial cells, the cells were fixed in ice cold 10% trichloroacetic acid (10 min) followed by incubations in 70%, 95%, and 100% ethanol for 3min each. Cells were rehydrated in PBS, blocked in 2% goat serum (1 h, room temperature) and incubated in anti-nitrotyrosine (1:100 dilution) for 2 h. Subsequent steps of the staining procedure were identical to the tissue staining. Color was developed with Vector Red substrate, and slides were mounted in glycerol.

In vitro studies in endothelial cells were performed by preparing cell as described in Gerritsen et al., Microcirculation 2: 151–163, (1995). In brief, lung microvascular endothelial cells were isolated from wild-type (+/+) and PARS knockout (–/–) mice. Cells were maintained in F12/DMEM (1:1) medium supplemented with endothelial cell growth supplement (100 μg/l heparin and 10% fetal calf serum).

Human umbilical vein endothelial cells (HUVEC) were obtained from ATCC and grown in F12 medium supplemented with endothelial cell growth supplement, 100 μg/l heparin and 10% fetal calf serum.

PARS activation was measured in endothelial cells seeded in 6 well tissue culture plates pre-coated with endothelial cell attachment factor (Sigma). Medium was replaced by regular- (see above) or FCS-free HUVEC medium containing 5 mM D-glucose 12 h before the experiment. Cells were pretreated with MnTBAP (100 μM), carboxy-PTIO (300 μM), L-NMMA (3 mM), L-NAME (3 mM) or PJ34 (0.1–3 μM) for 30 min followed by 6 h incubation in 30 mM glucose. At the end of incubation, medium was removed and PARS buffer [56 mM Hepes pH 7.5, 28 mM KCl, 28 mM NaCl, 2 mM $MgCl_2$, 0.01 % digitonin and 0.125 μM $^3$H-NAD (0.5 μCi/ml)] was added to the cells. After 10 min, cells were scraped, transferred into Eppendorf tubes and the reaction was stopped by trichloroacetic acid (TCA). Pellets were washed three times in 5% TCA and then solubilized in 500 μl 2% SDS/0.1 N NaOH at 37° C. Contents of the tubes were added to 7 ml ScintiSafe Plus scintillation liquid and radioactivity was measured in a liquid scintillation counter (Wallac, Gaithersburg, Md.). Activity was normalized for protein content.

High glucose concentration over 2–6 hours induced the activation of PARS in the murine endothelial cells, an effect not observed in the $PARS^{-/-}$ endothelial cells or in HUVECs treated with PJ34. The results are shown in FIGS. 2A–2E.

Figure 2A:
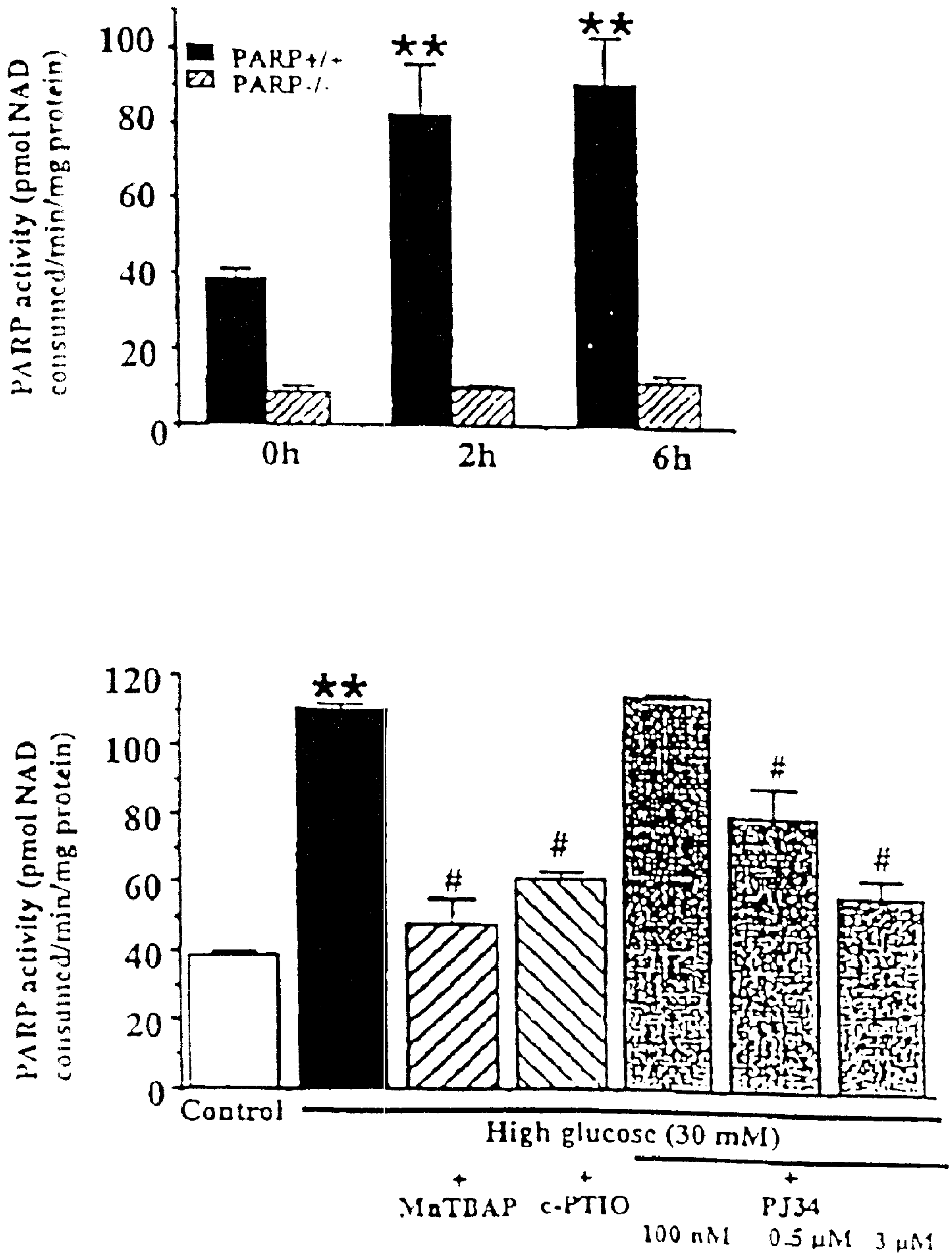
FIG. 2A is a histograms showing PARP activity over time in wild-type and PARS-deficient cells activity over time, and in cells exposed to low or high concentrations of glucose in endothelial cells from PARS.

FIG. 2A shows a time course of PARP activation and cell viability in wild-type and PARP deficient endothelial cells exposed to high glucose (30 mM), when compared to activity in normal culture medium (5 mM glucose). There was a significant, prolonged activation of PARP in response to high glucose. $PARP^{-/-}$ cells showed no detectable increase in PARP activity. The osmotic control (30 mM L-glucose) did not alter PARP activity. The right side of the figure shows the inhibitory effect of the cell-permeable superoxide dismutase mimic MnTBAP (100 μM), and the nitric oxide scavenger carboxy-PTIO (300 μM) and the inhibitory effect of the PARP inhibitor PJ34 (100 nM–3 μM) on high glucose induced PARP activation, at 6 hours.

Figure 2B:
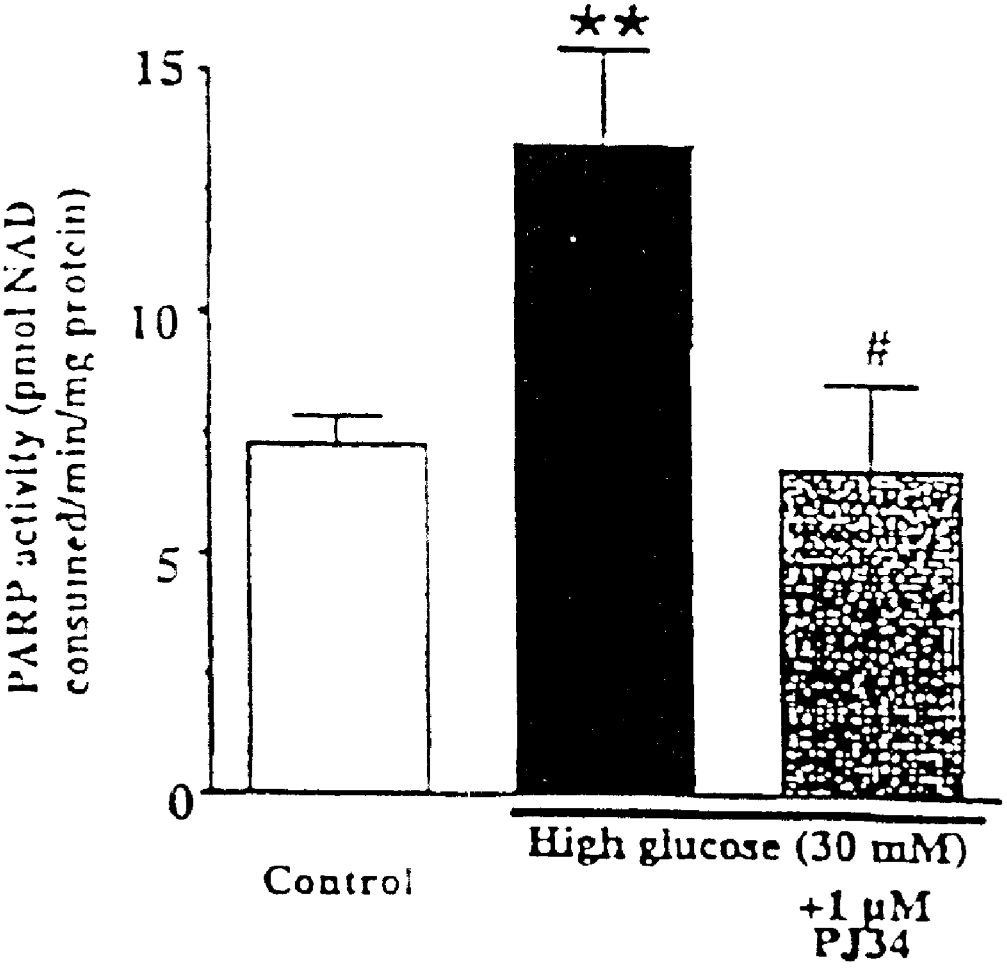
FIG. 2B is a histogram showing PARS activity in control cells, cells exposed to high concentrations of glucose (30 mM), and cells exposed to high concentrations of glucose and PJ34.

FIG. 2B shows activation of PARP in response to high glucose (30 mM), when compared to activity in normal culture medium (5 mM) in human umbilical vein endothelial cells (HUVECs) at 24 hours, and inhibitory effect of PJ34 (3 $\mu$M). The osmotic control (30 mM L-glucose) did not alter PARP activity or cell viability (not shown).

Tyrosine nitration was observed in endothelial cells maintained in normal culture medium (5 mM glucose) and in cells exposed to high glucose (30 mM). There was an intense nitrotyrosine staining in endothelial cells in high glucose, with a preferential perinuclear localization.

Figure 2C:
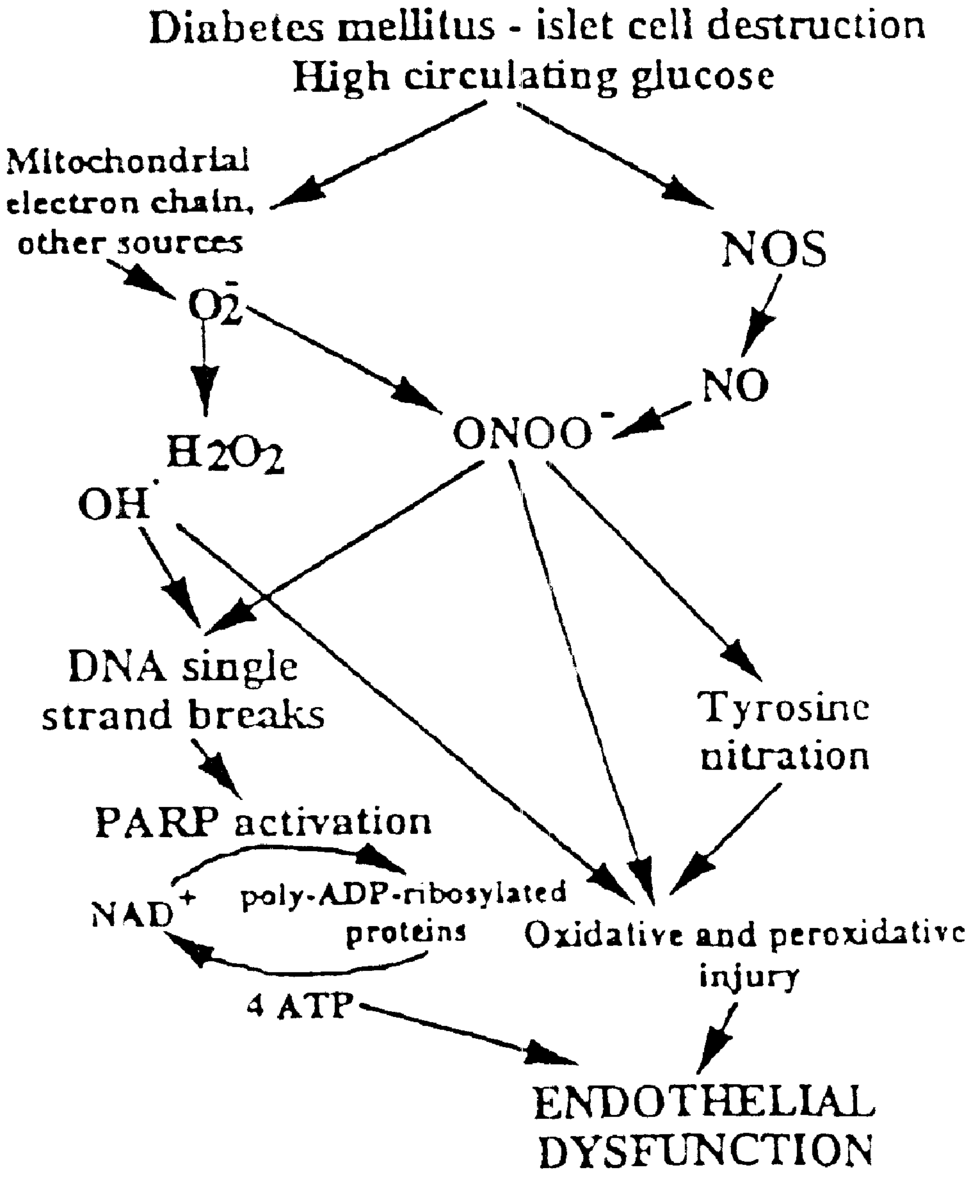
FIG. 2C is an illustration of a proposed scheme for the mechanism of PARP activation in diabetic blood vessels.
Figure 2D:
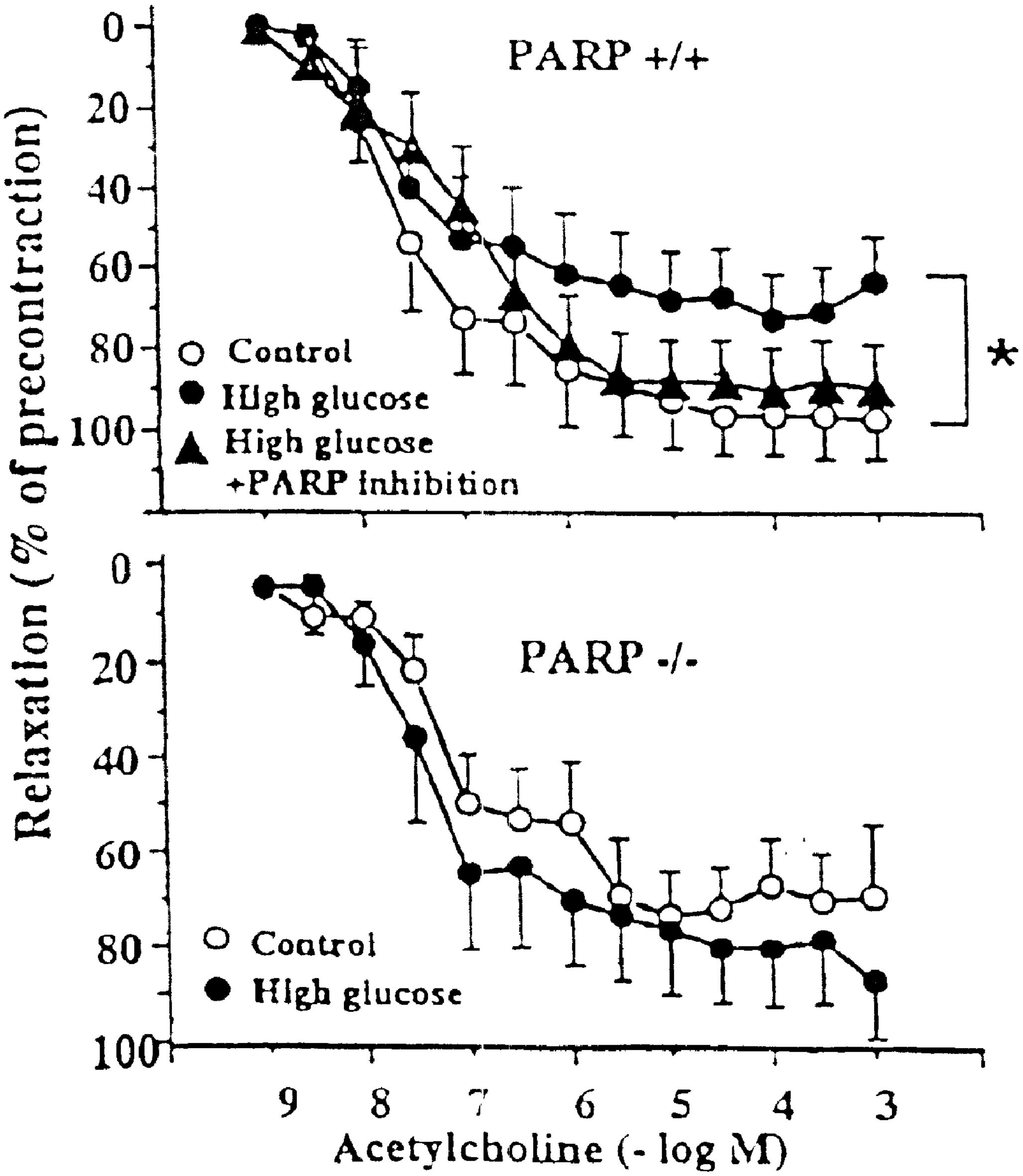
FIG. 2D is a graph showing the percentage relaxation of precontraction of endothelial cells in wild-type or PARS-deficient cells in varying concentrations of acetylcholine.

The development of endothelial dysfunction in thoracic aortic rings obtained from wild-type mice is illustrated in FIG. 2D. Rings incubated in 30 mM glucose for 16 hours showed an impairment in endothelium-dependent relaxation; an effect not seen in rings from $PARP^{-/-}$ mice, and an effect prevented by co-incubation of the wild-type rings with PJ34 (1 $\mu$M) in the presence of high glucose {"High glucose+PARP inhibition"). The osmotic control (30 mM L-glucose) did not alter endothelium-dependent relaxations (not shown). n=5–6 independent experiments, *p<0.05 between groups as indicated.

FIG. 2C shows a proposed scheme for the mechanism of PARP activation in diabetic blood vessels. Consistent with this scheme, high glucose induced the activation of PARS in human umbilical vein endothelial cells. PARS activation induced by high glucose concentration was prevented by PJ34, and was markedly reduced in mice of the PARS negative phenotype (FIGS. 2A and 2B). A small degree of increase in PARS activation (36% above control at 6 h of glucose incubation) was nevertheless also observed in the $PARS^{-/-}$ endothelial cells, which may be related to the existence of the various minor isoforms of PARS (see below), Similar to the in vivo situation in diabetes mellitus, tyrosine nitration was detected in the endothelial cells exposed to high glucose. PARS activation in response to high glucose was attenuated by MnTBAP, a cell-permeable water-soluble superoxide dismutase mimic, as well as by carboxy-PTIO, a nitric oxide scavenger compound, indicating that the activation of PARS is related to intravascular generation of reactive oxygen and nitrogen species (FIG. 2A). Similarly, pharmacological inhibition of cellular nitric oxide synthesis by $N^G$-methyl-L-arginine (L-NMA, 3 mM) or $N^G$-nitro-L-arginine methyl ester (L-NAME, 3 mM) significantly reduced the degree of PARS activation in endothelial cells exposed to high glucose.

Similar to the in vivo situation in hyperglycemia and diabetes, incubation of thoracic aortae from wild-type mice in high glucose concentration for 16 hours resulted in a significant loss of contractile and endothelium-dependent function. Vascular rings from the $PARS^{-/-}$ mice, on contrast, were fully resistant against high glucose induced endothelial dysfunction (FIG. 2C). Similarly, pharmacological inhibition of PARS also protected against the development of high glucose induced endothelial dysfunction (FIG. 2C). As in the ex vivo studies (see above), acetylcholine sensitivity of the rings incubated in high glucose was not altered by PARS inhibition or deficiency (not shown).

Example 9

Effect of the Substituted Phenanthridinone PJ34 on Transplanted Heart Function in an Animal Model System The effect of PARS inhibition on basal and acetylcholine-stimulated coronary blood flow in a rat heart transplantation model was examined using PJ34.

In this model, there is a transient suppression of myocardial blood flow and mechanical performance of the transplanted heart, which occurs as a result of external storage and subsequent reperfusion of the transplanted heart. Cardiac function is generally restored by 24 hours post-transplantation. Agents that are beneficial in this model accelerate recovery of the endothelial and cardiac function.

Studies were performed generally as described in Szabo et al., Cardiovasc. Res. 39: 683–90, 1998. Briefly, isogenic intra-abdominal heterotopic transplantation was performed in Lewis rats. After 1 hour of cold ischemic preservation, heart transplantation was performed. Circulation was restored either after application of placebo (control), or the PARS inhibitor PJ34 (3 mg/kg). An implanted balloon was used to obtain pressure-volume relations of the transplanted heart. Myocardial blood flow (MBF) was assessed by the hydrogen-clearance method. Measurements were taken after 1 and 24 h after transplantation. Endothelium-dependent vasodilation in response to acetylcholine (ACH) and endothelium-independent vasodilation in response to sodium nitroprusside were also determined.

Acetylcholine-induced vasodilation in transplanted or PJ34-treated hearts is shown in Tables 3 and 4. Effect of administration of the PARS inhibitor PJ34 (3 mg/kg i.v., immediately after the heart transplantation), on blood flow (basal and acetylcholine stimulated) in heretotropic rat hearts, at 1 h and 24 h after transplantation is shown. Inhibition of PARS with PJ34 markedly improved basal and acetylcholine stimulated coronary blood flow at 1 h after transplantation in this model. Administration of the PARS inhibitor PJ34 also markedly enhanced the myocardial performance (data not shown). The function of the hearts after lh was comparable to, e.g., not significantly different from, the function of the vehicle-treated hearts at 24 hours. These results demonstrate that inhibition of PARS brought about a near-complete functional recovery within 1 hour in this model of isogeneic heart transplant. These data indicate that inhibition of PARS by the compounds of the invention resulted in marked improvement of the function of the transplanted heart. Data shown represent N=5–6 per experimental group.

TABLE 3

| Basal coronary blood flow (ml/min) | | |
|---|---|---|
| Time | vehicle treated | PJ34 treated |
| 1 h after transplant | 2.8 ± 0.3 | 4.1 ± 0.4 |
| 24 h after transplant | 3.9 ± 0.3 | 4.2 ± 0.2 |

TABLE 4

| Acetylcholine stimulated coronary blood flow (ml/min) | | |
|---|---|---|
| Time | vehicle treated | PJ34 treated |
| 1 h after transplant | 3.5 ± 0.3 | 6.5 ± 0.5 |
| 24 h after transplant | 6.1 ± 0.4 | 8.2 ± 0.8 |

Other Embodiments

It is to be understood that while the invention has been described in conjunction with the detailed description thereof, the foregoing description is intended to illustrate and not limit the scope of the invention, which is defined by the scope of the appended claims.

What is claimed is:

1. A method for enhancing the vascular function of a transplanted organ in a subject, the method comprising administering to said subject a compound of Formula I:

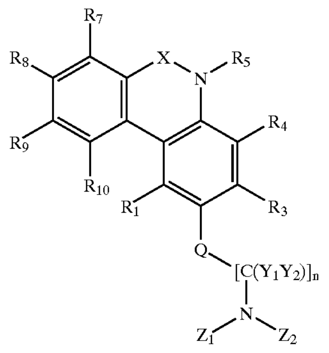

or a pharmaceutically acceptable base or acid addition salt, hydrate, ester, solvate, or a mixture thereof, wherein:

X is C═O;

Q is NHCO;

$R_1$, $R_3$, $R_4$, $R_5$, $R_7$, $R_8$, $R_9$, $R_{10}$, are, independently, hydrogen or lower alkyl;

$Y_1$ and $Y_2$ are hydrogen;

n is 0 to 10; and $Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members;

the compound being in an amount effective for enhancing the vascular function of a transplanted organ in said subject.

2. The method of claim 1, wherein $Z_1$ and $Z_2$ are methyl groups.

3. The method of claim 1, wherein $Z_1$ and $Z_2$ are ethyl groups.

4. The method of claim 1, wherein $Z_1$ and $Z_2$ are isopropyl groups.

5. The method of claim 1, wherein $Z_1$ is a methyl group and $Z_2$ is a benzyl group.

6. The method of claim 1, wherein N, $Z_1$ and $Z_2$ taken together, form a piperidine ring.

7. The method of claim 1, wherein $Z_1$, N, and $Z_2$ taken together form a fused ring having six ring members.

8. The method of claim 1, wherein said compound is administered intravenously, intraperitoneally, intramuscularly, intraventricularly, or orally.

9. The method of claim 1, wherein the transplanted organ is contacted with the compound prior to introduction of the organ into said subject.

10. The method of claim 1, wherein the compound is also administered to said subject in conjunction with the introduction of the organ into said subject.

11. The method of claim 1, wherein said subject is a human.

12. The method of claim 1, wherein the transplanted organ is selected from the group consisting of heart, kidney, lung, liver, retina, pancreatic islet, blood vessel, skin, and bone.

13. The method of claim 1, wherein the transplanted organ is a kidney.

14. The method of claim 1, wherein the transplanted organ is a heart.

15. The method of claim 1, wherein the compound is administered in combination with one or more immuno-suppressants.

16. The method of claim 15, wherein at least one of said immuno-suppressants is selected from the group consisting of cyclosporine, tacrolimus, mycophenolate mofetil, corticosteroids, and azathioprine.

17. The method of claim 1, wherein the compound is administered in combination with at least one organ preservative solution.

18. The method of claim 17, wherein said one or more organ preservative solution is selected from the group consisting of a histidine-tryptophan-alpha-ketoglutarate solution, Belzer's solution, Collin's solution, EP4, St. Thomas solution and a Stanford solution.

19. A method of enhancing the vascular function of a transplanted organ, the method comprising:

contacting an organ ex vivo with a compound of Formula I:

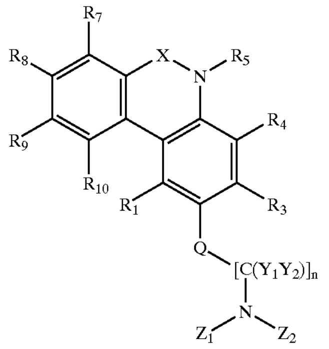

or a pharmaceutically acceptable base or acid addition salt, hydrate, ester, solvate, or a mixture thereof, wherein:

X is C═O;

Q is NHCO;

$R_1$, $R_3$, $R_4$, $R_5$, $R_7$, $R_8$, $R_9$, $R_{10}$, are, independently, hydrogen or lower alkyl;

$Y_1$ and $Y_2$ are hydrogen;

n is 0 to 10; and $Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members; and introducing said organ into a subject, the compound being in an amount effective for enhancing the vascular function of the organ.

20. A method for prolonging the function of a transplanted organ in a subject, the method comprising administering to said subject a compound of Formula I:

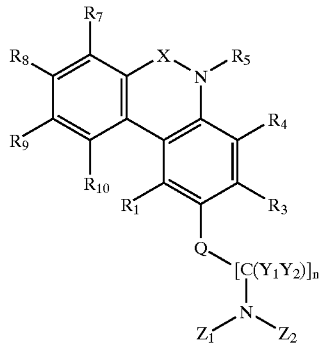

or a pharmaceutically acceptable base or acid addition salt, hydrate, ester, solvate, or a mixture thereof, wherein:

X is C═O;

Q is NHCO;

$R_1$, $R_3$, $R_4$, $R_5$, $R_7$, $R_8$, $R_9$, $R_{10}$, are, independently, hydrogen or lower alkyl;

$Y_1$ and $Y_2$ are hydrogen;

n is 0 to 10; and $Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members, the compound being in an amount effective for prolonging the function of a transplanted organ in said subject.

21. A method for enhancing the endothelial function of a transplanted organ in a subject, the method comprising administering to said subject a compound of Formula I:

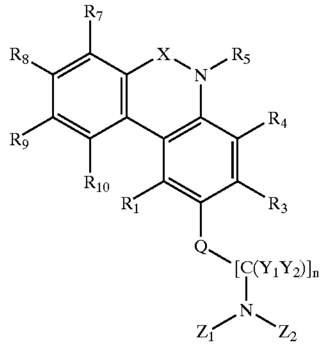

or a pharmaceutically acceptable base or acid addition salt, hydrate, ester, solvate, or a mixture thereof, wherein:

X is C═O;

Q is NHCO;

$R_1$, $R_3$, $R_4$, $R_5$, $R_7$, $R_8$, $R_9$, $R_{10}$, are, independently, hydrogen or lower alkyl;

$Y_1$ and $Y_2$ are hydrogen;

n is 0 to 10; and $Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members;

the compound being in an amount effective for enhancing the endothelial function of a transplanted organ in said subject.

22. The method of claim 21, wherein $Z_1$ and $Z_2$ are methyl groups.

23. The method of claim 21, wherein $Z_1$ and $Z_2$ are ethyl groups.

24. The method of claim 21, wherein $Z_1$ and $Z_2$ are isopropyl groups.

25. The method of claim 21, wherein $Z_1$ is a methyl group and $Z_2$ is a benzyl group.

26. The method of claim 21, wherein N, $Z_1$ and $Z_2$ taken together, form a piperidine ring.

27. The method of claim 21, wherein $Z_1$, N, and $Z_2$ taken together form a fused ring having six ring members.

28. The method of claim 21, wherein said compound is administered intravenously, intraperitoneally, intramuscularly, intraventricularly, or orally.

29. The method of claim 21, wherein the transplanted organ is contacted with the compound prior to introduction of the organ into said subject.

30. The method of claim 21, wherein the compound is administered to said subject in conjunction with the introduction of the organ into said subject.

31. The method of claim 21, wherein said subject is a human.

32. The method of claim 21, wherein the transplanted organ is selected from the group consisting of heart, kidney, lung, liver, retina, pancreatic islet, blood vessel, skin, and bone.

33. The method of claim 21, wherein the transplanted organ is a kidney.

34. The method of claim 21, wherein the transplanted organ is a heart.

35. The method of claim 21, wherein the compound is administered in combination with one or more immuno-suppressants.

36. The method of claim 35, wherein at least one of said immuno-suppressants is selected from the group consisting of cyclosporine, tacrolimus, mycophenolate mofetil, corticosteroids, and azathioprine.

37. The method of claim 21, wherein the compound is administered in combination with at least one organ preservative solution.

38. The method of claim 37, wherein said one or more organ preservative solution is selected from the group consisting of a histidine-tryptophan-alpha-ketoglutarate solution, Belzer's solution, Collin's solution, EP4, St. Thomas solution, and a Stanford solution.

39. A method of enhancing the endothelial function of a transplanted organ, the method comprising:

contacting an organ ex vivo with a compound of Formula I:

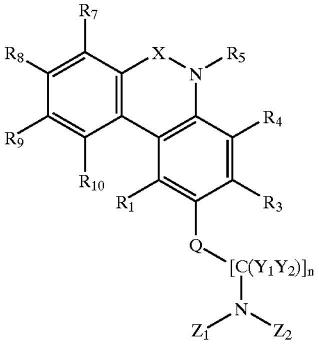

or a pharmaceutically acceptable base or acid addition salt, hydrate, ester, solvate, or a mixture thereof, wherein:

X is C═O;

Q is NHCO;

$R_1$, $R_3$, $R_4$, $R_5$, $R_7$, $R_8$, $R_9$, $R_{10}$, are, independently, hydrogen or lower alkyl;

$Y_1$ and $Y_2$ are hydrogen;

n is 0 to 10; and $Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members; and introducing said organ into a subject, the compound being in an amount effective for enhancing the endothelial function of a transplanted organ in said subject.

40. A method for prolonging the function of a transplanted organ, the method comprising:

contacting said organ ex vivo with a compound of Formula I:

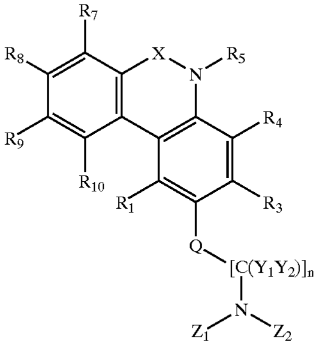

or a pharmaceutically acceptable base or acid addition salt, hydrate, ester, solvate, or a mixture thereof, wherein:

X is C═O;

Q is NHCO;

$R_1$, $R_3$, $R_4$, $R_5$, $R_7$, $R_8$, $R_9$, $R_{10}$, are, independently, hydrogen or lower alkyl;

$Y_1$ and $Y_2$ are hydrogen;

n is 0 to 10; and $Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members, the compound being in an amount effective for prolonging the function of the organ.

41. The method of claim 20, 39 or 40, wherein said compound is administered intravenously, intraperitoneally, intramuscularly, intraventricularly, or orally.

42. The method of claim 20, 39 or 40, wherein the transplanted organ is contacted with the compound prior to introduction of the organ into said subject.

43. The method of claim 20, 39 or 40, wherein the compound is also administered to said subject in conjunction with the introduction of the organ into said subject.

44. The method of claim 20, 39 or 40, wherein said subject is a human.

45. The method of claim 19, 20, 39 or 40, wherein the transplanted organ is selected from the group consisting of heart, kidney, lung, liver, retina, pancreatic islet, blood vessel, skin, and bone.

46. The method of claim 19, 20, 39 or 40, wherein the transplanted organ is a kidney.

47. The method of claim 19, 20, 39 or 40, wherein the transplanted organ is a heart.

48. The method of claim 19, 20, 39 or 40, wherein the compound is administered in combination with one or more immuno-suppressants.

49. The method of claim 48, wherein at least one of said immuno-suppressants is selected from the group consisting of cyclosporine, tacrolimus, mycophenolate mofetil, corticosteroids, and azathioprine.

50. The method of claim 19, 20, 39 or 40, wherein the compound is administered in combination with at least one organ preservative solution.

51. The method of claim 50, wherein said one or more organ preservative solution is selected from the group consisting of a histidine-tryptophan-alpha-ketoglutarate solution, Belzer's solution, Collin's solution, EP4, St. Thomas solution, and a Stanford solution.

52. The method of claim 19, 20, 39 or 40, wherein $Z_1$ and $Z_2$ are methyl groups.

53. The method of claim 19, 20, 39 or 40, wherein $Z_1$ and $Z_2$ are ethyl groups.

54. The method of claim 19, 20, 39 or 40, wherein $Z_1$ and $Z_2$ are isopropyl groups.

55. The method of claim 19, 20, 39 or 40, wherein $Z_1$ is a methyl group and $Z_2$ is a benzyl group.

56. The method of claim 19, 20, 39 or 40, wherein N, $Z_1$ and $Z_2$ taken together, form a piperidine ring.

57. The method of claim 19, 20, 39 or 40, wherein $Z_1$, N, and $Z_2$ taken together form a fused ring having six ring members.

58. The method of claim 1, 19, 20, 21, 39 or 40, wherein $Z_1$ and $Z_2$ are methyl groups and $R_1$, $R_3$, $R_4$, $R_5$, $R_7$, $R_8$, $R_9$ and $R_{10}$ are hydrogen.

59. The method of claim 1, 19, 20, 21, 39 or 40, wherein $Z_1$ and $Z_2$ are ethyl groups and $R_1$, $R_3$, $R_4$, $R_5$, $R_7$, $R_8$, $R_9$ and $R_{10}$ are hydrogen.

* * * * *

UNITED STATES PATENT AND TRADEMARK OFFICE

CERTIFICATE OF CORRECTION

PATENT NO. : 6,476,048 B1
DATED : November 5, 2002
INVENTOR(S) : Szabo et al.

It is certified that error appears in the above-identified patent and that said Letters Patent is hereby corrected as shown below:

Title page,
Item [63], "6,297,990" should be -- 6,277,990 --.

Column 1,
Line 7, "6,297,990" should be -- 6,277,990 --.

Signed and Sealed this

Twenty-ninth Day of July, 2003

JAMES E. ROGAN
*Director of the United States Patent and Trademark Office*